(12) United States Patent
Kimmerling et al.

(10) Patent No.: US 12,362,038 B2
(45) Date of Patent: Jul. 15, 2025

(54) IDENTIFYING CANCER THERAPIES

(71) Applicant: Travera, Inc., Medford, MA (US)

(72) Inventors: Rob Kimmerling, Cambridge, MA (US); Selim Olcum, Cambridge, MA (US); Clifford Reid, Pacifica, CA (US); Mark Stevens, Cambridge, MA (US)

(73) Assignee: Travera, Inc., Medford, MA (US)

( * ) Notice: Subject to any disclaimer, the term of this patent is extended or adjusted under 35 U.S.C. 154(b) by 426 days.

(21) Appl. No.: 16/739,667

(22) Filed: Jan. 10, 2020

(65) Prior Publication Data

US 2020/0227136 A1 Jul. 16, 2020

Related U.S. Application Data

(60) Provisional application No. 62/790,735, filed on Jan. 10, 2019.

(51) Int. Cl.
*G16H 10/40* (2018.01)
*G01N 33/50* (2006.01)
(Continued)

(52) U.S. Cl.
CPC ......... *G16B 20/00* (2019.02); *G01N 33/5011* (2013.01); *G01N 33/5067* (2013.01);
(Continued)

(58) Field of Classification Search
None
See application file for complete search history.

(56) References Cited

U.S. PATENT DOCUMENTS 1,007,028 A 10/1911 Gilbert
4,683,195 A 7/1987 Mullis et al.
(Continued)

FOREIGN PATENT DOCUMENTS

| FR | 2996219 A1 | 4/2014 |
|---|---|---|
| JP | 2007-506977 A | 3/2007 |
| JP | 2013-543127 A | 11/2013 |
| JP | 2014-006211 A | 1/2014 |
| JP | 2014-510921 A | 5/2014 |
| WO | 2012/059828 A2 | 5/2012 |

(Continued)

OTHER PUBLICATIONS

"Supporting mass accumulation rate (MAR) as a predictive biomarker in multiple myeloma"—a clinical trial to study mass accumulation rate as a biomarker of patient response to a treatment regimen; Dec. 17, 2018; Clinical Trials.gov. (Year: 2018).*

(Continued)

*Primary Examiner* — John A Pauls
(74) *Attorney, Agent, or Firm* — Thomas C. Meyers; Sullivan & Worcester LLP

(57) ABSTRACT

In silico tools are used to determine possibly effective therapies for treating a patient's cancer based on patient, drug, and cancer information. Functional assays can be performed on living cancer cells from the patient to evaluate the possibly effective therapies along with subsequent genomic or other more destructive assays to provide additional information from a single sample. Drug, patient, cancer, and outcome information can be recorded and updated iteratively and analyzed using machine learning to identify correlations between various patient, cancer, and drug characteristics and expected outcomes and drug efficacies.

17 Claims, 7 Drawing Sheets

(51) Int. Cl.
  *G16B 20/00* (2019.01)
  *G16H 50/20* (2018.01)
  *G16H 50/30* (2018.01)
(52) U.S. Cl.
  CPC ............ *G16H 10/40* (2018.01); *G16H 50/20* (2018.01); *G01N 2800/52* (2013.01); *G01N 2800/60* (2013.01); *G16H 50/30* (2018.01)

(56) References Cited

U.S. PATENT DOCUMENTS

| | | | |
|---|---|---|---|
| 4,683,202 | A | 7/1987 | Mullis |
| 6,210,891 | B1 | 4/2001 | Nyren et al. |
| 6,223,128 | B1 | 4/2001 | Allex et al. |
| 6,235,501 | B1 | 5/2001 | Gautsch et al. |
| 6,306,597 | B1 | 10/2001 | Macevicz |
| 6,719,449 | B1 | 4/2004 | Laugharn, Jr. et al. |
| 6,828,100 | B1 | 12/2004 | Ronaghi |
| 6,833,246 | B2 | 12/2004 | Balasubramanian |
| 6,911,345 | B2 | 6/2005 | Quake et al. |
| 6,948,843 | B2 | 9/2005 | Laugharn, Jr. et al. |
| 7,215,214 | B1 | 5/2007 | Taheri et al. |
| 7,232,656 | B2 | 6/2007 | Balasubramanian et al. |
| 7,260,980 | B2* | 8/2007 | Adams ................ G01Q 60/42 |
| | | | 73/61.49 |
| 7,387,889 | B2 | 6/2008 | Manalis |
| 7,449,968 | B1 | 11/2008 | Cioffi et al. |
| 7,598,035 | B2 | 10/2009 | Macevicz |
| 7,640,051 | B2 | 12/2009 | Krishnan et al. |
| 7,809,509 | B2 | 10/2010 | Milosavljevic |
| 7,812,680 | B1 | 10/2010 | Brown et al. |
| 7,835,871 | B2 | 11/2010 | Kain et al. |
| 7,838,284 | B2 | 11/2010 | Manalis |
| 7,960,120 | B2 | 6/2011 | Rigatti et al. |
| 8,087,284 | B2 | 1/2012 | Babcock et al. |
| 8,165,821 | B2 | 4/2012 | Zhang |
| 8,209,130 | B1 | 6/2012 | Kennedy et al. |
| 8,291,750 | B1 | 10/2012 | Goodbread et al. |
| 8,418,535 | B2 | 4/2013 | Manalis et al. |
| 8,639,043 | B2 | 1/2014 | Levenson et al. |
| 8,722,419 | B2 | 5/2014 | Manalis et al. |
| 8,929,849 | B1 | 1/2015 | Dudziak |
| 9,027,388 | B2 | 5/2015 | Babcock et al. |
| 9,132,294 | B2 | 9/2015 | Zheng et al. |
| 9,134,294 | B2 | 9/2015 | Manalis et al. |
| 9,134,295 | B1 | 9/2015 | Delgado et al. |
| 9,347,815 | B2 | 5/2016 | Roukes et al. |
| 9,515,608 | B2 | 12/2016 | Gourlat et al. |
| 9,558,399 | B1 | 1/2017 | Jeka et al. |
| 9,709,400 | B2 | 7/2017 | Kapusta |
| 9,757,727 | B2 | 9/2017 | Manalis et al. |
| 2002/0164825 | A1* | 11/2002 | Chen ................ G01N 33/57488 |
| | | | 436/526 |
| 2003/0033876 | A1 | 2/2003 | Roukes et al. |
| 2003/0062473 | A1 | 4/2003 | Weinberger et al. |
| 2003/0176174 | A1 | 9/2003 | Seppinen et al. |
| 2004/0193019 | A1* | 9/2004 | Wei ................ G16H 50/70 |
| | | | 600/300 |
| 2004/0235198 | A1* | 11/2004 | Marx ................ G01N 33/54373 |
| | | | 436/63 |
| 2005/0064581 | A1 | 3/2005 | Manalis et al. |
| 2005/0074793 | A1* | 4/2005 | Wilson ............ G01N 33/57484 |
| | | | 435/7.1 |
| 2005/0112590 | A1 | 5/2005 | Boom et al. |
| 2005/0164236 | A1 | 7/2005 | Su et al. |
| 2005/0186969 | A1 | 8/2005 | Lohtia |
| 2006/0014157 | A1* | 1/2006 | Kawabe ................ A61P 35/00 |
| | | | 435/6.14 |
| 2006/0024681 | A1 | 2/2006 | Smith et al. |
| 2006/0292611 | A1 | 12/2006 | Berka et al. |
| 2007/0114362 | A1 | 5/2007 | Feng et al. |
| 2007/0176705 | A1 | 8/2007 | Sutardja |
| 2007/0178529 | A1 | 8/2007 | Breidford et al. |
| 2009/0014360 | A1 | 1/2009 | Toner et al. |
| 2009/0044608 | A1 | 2/2009 | Babcock et al. |
| 2009/0053749 | A1* | 2/2009 | Manalis ............ G01N 15/1056 |
| | | | 435/287.1 |
| 2009/0261241 | A1 | 10/2009 | Roukes et al. |
| 2009/0318310 | A1 | 12/2009 | Liu et al. |
| 2010/0033723 | A1* | 2/2010 | Thundat ............ G01N 21/1702 |
| | | | 356/432 |
| 2010/0075628 | A1 | 3/2010 | Ye |
| 2010/0154535 | A1 | 6/2010 | Manalis et al. |
| 2010/0227310 | A1 | 9/2010 | Manalis et al. |
| 2010/0263445 | A1 | 10/2010 | Hayner et al. |
| 2010/0288043 | A1* | 11/2010 | Manalis ................ G01N 15/00 |
| | | | 73/32 R |
| 2010/0304989 | A1* | 12/2010 | Von Hoff ............ G16H 50/20 |
| | | | 506/9 |
| 2010/0315138 | A1 | 12/2010 | Namba et al. |
| 2011/0009278 | A1 | 1/2011 | Kain et al. |
| 2011/0113856 | A1 | 5/2011 | Cobianu et al. |
| 2011/0218839 | A1 | 9/2011 | Shamaiengar |
| 2011/0257889 | A1 | 10/2011 | Klammer et al. |
| 2011/0271412 | A1 | 11/2011 | Rychen |
| 2012/0013475 | A1 | 1/2012 | Farley et al. |
| 2013/0132438 | A1 | 5/2013 | Park et al. |
| 2013/0210647 | A1 | 8/2013 | Kassis |
| 2013/0244686 | A1 | 9/2013 | Saha et al. |
| 2013/0268290 | A1 | 10/2013 | Jackson et al. |
| 2013/0268474 | A1 | 10/2013 | Nizzari et al. |
| 2013/0304894 | A1 | 11/2013 | Kim |
| 2014/0013848 | A1 | 1/2014 | Colinet et al. |
| 2014/0156224 | A1 | 6/2014 | Roukes et al. |
| 2014/0236759 | A1 | 8/2014 | Mirabile |
| 2014/0306623 | A1 | 10/2014 | Caffee et al. |
| 2014/0312980 | A1 | 10/2014 | Villard et al. |
| 2015/0032264 | A1 | 1/2015 | Emmons et al. |
| 2015/0067351 | A1 | 3/2015 | Wang et al. |
| 2015/0285789 | A1* | 10/2015 | Montano ............ G01N 33/5073 |
| | | | 506/10 |
| 2015/0300999 | A1 | 10/2015 | Andreucci et al. |
| 2015/0308990 | A1 | 10/2015 | Andreucci et al. |
| 2015/0343444 | A1 | 12/2015 | Manalis et al. |
| 2016/0044467 | A1 | 2/2016 | Clausen |
| 2016/0091544 | A1 | 3/2016 | Daneshmand et al. |
| 2016/0123858 | A1 | 5/2016 | Kapur et al. |
| 2016/0174032 | A1 | 6/2016 | Xin et al. |
| 2016/0174902 | A1 | 6/2016 | Georgescu et al. |
| 2016/0181977 | A1 | 6/2016 | Gourlat et al. |
| 2016/0210647 | A1 | 7/2016 | Chang et al. |
| 2016/0224760 | A1 | 8/2016 | Peták et al. |
| 2017/0053398 | A1 | 2/2017 | Mahoor et al. |
| 2017/0103183 | A1* | 4/2017 | Flobak ................ B82Y 40/00 |
| 2017/0117905 | A1* | 4/2017 | Cermak ................ H03L 7/00 |
| 2017/0176478 | A1 | 6/2017 | Harbers et al. |
| 2017/0185730 | A1* | 6/2017 | McIntyre ................ G06N 5/01 |
| 2017/0260590 | A1* | 9/2017 | Eltoukhy ............ G16B 30/00 |
| 2018/0004905 | A1* | 1/2018 | Szeto ................ G16H 50/20 |
| 2018/0043082 | A1* | 2/2018 | Leinenbach ........ A61M 1/3496 |
| 2018/0207639 | A1 | 7/2018 | Butler et al. |
| 2018/0299362 | A1 | 10/2018 | Kimmerling et al. |
| 2020/0411199 | A1* | 12/2020 | Shrager ................ G16H 10/20 |

FOREIGN PATENT DOCUMENTS

| | | | | |
|---|---|---|---|---|
| WO | 2012/172204 | A1 | 12/2012 | |
| WO | 2015/155044 | A1 | 10/2015 | |
| WO | WO-2016069634 | A1 * | 5/2016 | ............ G01H 13/00 |
| WO | 2016/094330 | A2 | 6/2016 | |
| WO | 2016/182551 | A1 | 11/2016 | |
| WO | 2018/236708 | A1 | 12/2018 | |
| WO | WO-2020102595 | A1 * | 5/2020 | ......... G01N 33/5017 |

OTHER PUBLICATIONS

"Drug sensitivity of single cancer cells is predicted by changes in mass accumulation rate"; Stevens et al. Oct. 10, 2016; Nat Biotechnol. (Year: 2016).*

Georgatos, 1997, Nuclear envelope breakdown in mammalian cells involves stepwise lamina disassembly and microtubule-drive deformation of the nuclear membrane, J Cell Sci, 110( Pt 17):2129-40.

(56) References Cited

OTHER PUBLICATIONS

Gerhardt, 1961, Permeability of bacterial spores. II. Molecular variables affecting solute permeation, J Bacterial, 82:750-60.
Godin, 2010, Using buoyant mass to measure the growth of single cells, Nat Methods, 7(5):387-90, total of (9 pages).
Goldstein, 2014, Faculty profile: Scott Manalis, MIT BE Newsletter (3 pages).
Gossett, 2012, Hydrodynamic stretching of single cells for large population mechanical phenotyping, Proc Natl Acad Sci U S A, 15;109(20):7630-5.
Green, 2012, Molecular Cloning: A Laboratory Manual 4th edition, Cold Spring Harbor Laboratory Press, Cold Spring Harbor, NY, (2028 pages).
Grover, 2011, Measuring single-cell density, Proc Natl Acad Sci U S A, 108(27):10992-6.
Guillou, 2016, Dynamic monitoring of cell mechanical properties using profile microindentation, Sci Rep, 6:21529(1-13).
Guo, 2017, Cell volume change through water efflux impacts cell stiffness and stem cell fate, Proc Natl Acad Sci U S A, 114(41):E8618-E8627.
Gupta, 2017, Equilibrium and out-of-equilibrium mechanics of living mammalian cytoplasm, J Meehan Phys Solids, 107:284-93.
Hanay, 2012, Single-protein nanomechanical mass spectrometry in real time, Nat Nanotechnol, 7(9):602-8.
Hartono, 2011, On-chip measurements of cell compressibility via acoustic radiation, Lab Chip, 11(23):4072-80.
Henderson, 1992, Actin filament dynamics in living glial cells imaged by atomic force microscopy, Science, 257 (5078):1944-6.
Hiramoto, 1974, Mechanical properties of the surface of the sea urchin egg at fertilization and during cleavage. Exp Cell Res, 89(2):320-6.
Hogenauer, 1981, An economical class of digital filters for decimation and interpolation, IEEE Trans on Acousitics, Speech, and Signal Processing, 29(2):155-62.
International Preliminary Report on Patentability issued in International Application No. PCT/US2015/057634, date of mailing: Jan. 22, 2016 (6 pages).
International Preliminary Report on Patentability issued in International Application No. PCT/US2018/0258040, date of mailing: Oct. 10, 2019 (7 pages).
International Preliminary Report on Patentability issued in International Application No. PCT/US2018/037995, date of mailing: Jan. 2, 2020 (8 pages).
International Search Report and Written Opinion issued in International Application No. PCT/US2015/057634, date of mailing: Jan. 22, 2016 (10 pages).
International Search Report and Written Opinion issued in International Application No. PCT/US2018/025040, date of mailing: Jun. 8, 2018 (12 pages).
International Search Report and Written Opinion issued in International Application No. PCT/US2018/037995, date of mailing: Aug. 27, 2018 (12 pages).
International Search Report and Written Opinion issued in International Application No. PCT/US2020/013089, date of mailing: Apr. 8, 2020 (7 pages).
International Search Report and Written Opinion issued in International Application No. PCT/US2020/13096, date of mailing: Apr. 9, 2020 (14 pages).
Ivanova, 2013, Bactericidal activity of black silicon. Nat Commun, 4:2838(1-7).
Jin, 2015, A microfluidic device enabling high-efficiency single cell trapping, Biomicrofluidics, 9:014101(1-16).
Kang, 2019, Noninvasive monitoring of single-cell mechanics by acoustic scattering, Nat Methods (12 pages).
Khalili, 2016, A microfluidic device for hydrodynamic trapping and manipulation platform of a single biological cell, Appl Sci, 6(40):1-17.
Kimmerling, 2016, A microfluidic platform enabling single-cell RNA-seq of multigenerational lineages, Nat Commun, 7:10220(1-7).
Kimmerling, 2017, A toolset for linking phenotype and gene expression at the single-cell level. Doctoral Thesis-Massachusetts Institute of Technology, (142 pages).
Kimmerling, 2018, Linking single-cell measurements of mass, growth rate, and gene expression, bioRxiv.com (19 pages).
Knudsen, 2016, Water and small-molecule permeation of dormant Bacillus subtilis spores, J Bacterial, 98(1):168-77.
Kobayashi, 2009, Frequency noise in freuency modulation atomic force microscopy, Rev Sci Instrum, 80(4):043708 (1-8).
Kouh, 2005, Room-temperature operation of a nanoelectromechanical resonator embedded in a phase-locked loop, Appl Phys Lett, 87(11):113112(1-3).
Kumar, 2010, Comparing de novo assemblers for 454 transcriptome data, Genomics 11:571 (12 pages).
Kundu, 1991, Measuring elastic properties of cells by evaluation of scanning acoustic microscopy V(Z) values using simplex algorithm, Biophys J. 59(6):1194-207.
Lee, 2010, Toward attogram mass measurements in solution with suspended nanochannel resonators, Nano Lett, 10(7):257-42.
Lee, 2011, High precision particle mass sensing using microchannel resonators in the second vibration mode, Rev Sci Instrum, 82(023704):1-4.
Lee, 2011, Suspended microchannel resonators with piezoresistive sensors, The Royal Society of Chemistry, UK, Lap Chip, 11:645-51.
Li, 2009, Fast and accurate short read alignment with Burrows-Wheeler Transform, Bioinformatics 25:1754-1760.
Li, 2009, The Sequence alignment/map (SAM) format and SAMtools, Bioinformatics 25:2078-2079.
Li, 2011, Improving SNP discovery by base alignment quality, Bioinformatics 27,1157-1158.
Lim, 2006, Mechanical models for living cells—a review, J Biomech, 39(2):195-216.
Lin, 2008, Zoom! Zillions Of Oligos Mapped, Bioinformatics 24:2431-2437.
Lincoln, 2007, High-throughput rheological measurements with an optical stretcher, Methods Cell Biol, 83:397-423.
Luskin, 2018, Targeting minimal residual disease: a path to cure?, Nat Rev Cancer, 18:255-263.
Manak, 2018, Live-cell phenotypic-biomarker microfluidic assay for the risk stratification of cancer patients via machine learning, Nat Biomed Eng, 2(10): entire document esp. p. 1, p. 3, p. 6, p. 8, p. 17.
Matzke, 2001, Direct, high-resolution measurement of furrow stiffening during division of adherent cells, Nat Cell Biol, 3(6):607-10.
McKenna, 2010, The Genome Analysis Toolkit: a MapReduce framework for analyzing next-generation DNA sequencing data, Genome Res, 20(9):1297-1303.
Miyoshi, 2015, Etiology of Ascites and Pleural Effusion Associated with Ovarian Tumors: Literature Review and Case Reports of Three Ovarian Tumors Presenting with Massive Ascites, but without Peritoneal Dissemination, Case Reports in Obstetrics and Gynecology, Article ID 414019, (5 pages).
Narang, 1977, Improved Phosphotriester Method for the Synthesis of Gene Fragments, Methods Enzymol, 68:90-98.
Albrecht, 1991, Frequency modulation detection using high-Q cantilevers for enhanced force microscope snesitivity, J Appl Phys, 69(2):668-73.
AlexNet Krizhevsky, 2012, Imagenet classification with deep convolutional neural networks, in Pereira, et al., Eds. Advances in Neural Information Processing Systems 25, 9 pages.
Ananthakrishnan, 2006, Quantifying the contribution of actin networks to the elastic strength of fibroblasts, J Theor Biol, 242(2):502-16.
Antonarakis, 1998, Recommendations for a nomenclature system for human gene mutations, Human Mutations 11:1-3.
Atia, 1997, A phase-locked shear-force microscope for distance regulation in near-field optical microscopy, App Phys Lett, 70(4):405-7.
Bagnall, 2016, Deformability-based cell selection with downstream immunofluorescence analysis, Integr Biol (Camb), 8(5):654-64.
Balland, 2006, Power laws in microrheology experiments on living cells: Comparative analysis and modeling, Phys Rev E Stat Nonlin Soft Matter Phys, 74(2 Pt1):021911(1-17).

(56) References Cited

OTHER PUBLICATIONS

Ben-Hur, 2001, Support Vector Clustering, Journal of Machine Learning Research, 2:125-137.
Bouloc, 2011, FPGA-based prgrammable digital PLL with very high frequency resolution, 2011 18th IEEE Intl Conf on Electronics, Circuits, and Systems, 370-3.
Bouloc, 2012, All digital control system for a novel high frequency force sensor in non contact atomic force microscopy, IEEE Sensors, 1-4.
Brangwynne, 2007, Force fluctuations and polymerization dynamics of intracellular microtubules, Proc Natl Acad Sci U S A, 104(41):16128-33.
Breiman, 2001, Random Forests, Machine Learning 45:5-32.
Bremer, 2008, Modulation of chemical composition and other parameters of the cell at different exponential growth rates, EcoSal Plus, 3(1):1-49.
Brown, 1979, Chemical synthesis and cloning of a tyrosine tRNA gene, Methods Enzymol, 68:109-51.
Bruus, 2011, Acoustofluidics 1: Governing equations in microfluidics, Lab Chip, 11(22):3742-51.
Bryan, 2010, Measurement of mass, density, and volume during the cell cycle of yeast, Proc Natl Acad Sci U S A, 107(3):999-1004.
Bryan, 2014, Measuring single cell mass, volume and density with dual suspended microchannel resonators, Lab Chip, 14(3):569-576.
Burg, 2007, Weighing of biomolecules, single cells and single nanoparticles in fluid, Nature, 446:1066-1069.
Burg, 2009, Nonmonotonic energy dissipation in microfluidic resonators, Phys Rev Lett, 102(22):228103(1-4).
Butzin, 2012, Analysis of the effects of a gerP mutation on the germination of spores of Bacillus subtilis, J Bacterial, 194(21):5749-58.
Byun, 2013, Characterizing deformability and surface friction of cancer cells, Proc Natl Acad Sci U S A, 110(19):7580-5.
Byun, 2015, Characterizing cellular biophysical responses to stress by relating density, deformability, and size, Biophys J, 109(8):1565-73.
Calistri, 2018, Microfluidic active loading of single cells enables analysis of complex xlinical specimens, Nat Com (39 pages).
Cartagena-Rivera, 2016, Actomyosin cortical mechanical properties in nonadherent cells determined by atomic force microscopy, Biophys J, 110(11):2528-2539.
Cermak, 2016, High-throughput measurement of single-cell growth rates using serial microfluidic mass sensor arrays, Nat Biotech 34(10):1052-1059.
Cermak, 2017, Direct single-cell biomass estimates for marine bacteria via Archimedes' principle, ISME J, 1(3):825-828.
Cetin, 2017, Determining therapeutic susceptibility in multiple myeloma by single-cell massaccumulation, Nat Commun, 8(1):1613 (12 pages).
Chaste, 2012, A nanomechanical mass sensor with yoctogram resolution, Nat Nanotechnol, 7(5):301-4.
Chen, 2016, XGBoost: A Scalable Tree Boosting System, 22nd SIGKDD Conference on Knowledge Discovery and Data Mining, pp. 785-794.
Chugh, 2017, Actin cortex architecture regulates cell surface tension, Nat Cell Biol, 19(6):689-697 (Suppl Info 19 pages).
Clark, 2013, Monitoring actin cortex thickness in live cells, Biophys J, 105(3):570-80.
Criminisi, 2012, Decision Forests: A Unified Framework for Classification, Regression, Density Estimation, Manifold Learning and Semi-Supervised Learning, Foundations and Trends in Computer Graphics and Vision 7(2-3):81-227.
Cunningham, 2010, Tissue disaggregation, Methods Mol Biol, 588:327-330.
Danecek, 2011, The variant call format and VCFtools, Bioinformatics 27(15):2156-2158.
De Dunnen, 2003, Mutation Nomenclature, Curr Prot Hum Genet, 109:121-124.
Delgado, 2013, Intracellular water exchange for measuring the dry mass, water mass and changes in chemical composition of living cells, PLoS One, 8(7):e67590(1-11).
Dendukuri, 2006, Continuous-flow lithography for high-throughput microparticle synthesis, Nat Mater, 5(5):365-9.
Dendukuri, 2007, Stop-flow lithography in a microfluidic device, Lab Chip, 7(7):818-28.
Dextras, 2009, Integrated measurement of the mass and surface charge of discrete microparticles using a suspended microchannel resonator, Anal Chem, 81:4517-23.
Di Carlo, 2007, Continuous inertial focusing, ordering, and separation of particles in microchannels, Proc Natl Acad Sci, 104(48):18892-7.
Dieffenbach, 1995, PCR Primer, a Laboratory Manual, Cold Spring Harbor Press, Plainview, NY.
DiGuistini, 2009, De novo sequence assembly of a filamentous fungus using Sanger, 454 and Illumina sequence data, Genome Biology, 10:R94 (12 pages).
Dohn, 2007, Mass and position determination of attached particles on cantilever based mass sensors, Rev Sci Instrum, 78(10):103303 (4 pages).
Dohn, 2010, Position and mass determination of multiple particles using cantilever based mass sensors, Appl Phys Lett, 97(4):044103 (4 pages).
Ekinci, 2004, Ultimate limits to inertial mass sensing based upon nanoelectromechanical systems, J Appl Phys, 95(5):2682-9.
Fischer-Friedrich, 2016, Rheology of the active cell cortex in mitosis, Biophys J, 111(3):589-600.
Freund, 1997, A decision-theoretic generalization of on-line learning and an application to boosting, Journal of Computer and System Sciences, 55:119-139.
Friedman, 2015, Precision medicine for cancer with next-generation functional diagnostics, Nat Rev Cancer 15(12):747-756.
Gardel, 2010, Mechanical integration of actin and adhesion dynamics in cell migration, Annu Rev Cell Dev Biol, 26:315-33.
Gavartin, 2013, Stabilizaton of a linear nanomechanical oscillator to its thermodynamic limit, Nat Commun, 4:2860(1-8).
Narayanamurthy, 2017, Microfluidic hydrodynamic trapping for single cell analysis: mechanisms, methods and applications, Anal Methods, 9:3751-72.
Ning, 2001, SSAHA: A fast search method for large DNA database, Genome Research, 11(10):1725-9.
Olcum, 2014, Weighing nanoparticles in solution at the attogram scale, Proc Natl Acad Sci USA, 111(4):1310-5.
Olcum, 2015, High-speed multiple-mode mass-sensing resolves dynamic nanoscale mass distributions, Nat Commun, 6:7070(1-8).
Otto, 2015, Real-time deformability cytometry: on-the-fly cell mechanical phenotyping, Nat Methods, 12(3):199-202.
Ou-Yang, 2010, Complex fluids: Probing mechanical properties of biological systems with optical tweezers, Annu Rev Phys Chem, 61:421-40.
Paluch, 2009, Biology and physics of cell shape changes in development, Curr Biol, 19(17):R790-9.
Plomp, 2014, Architecture and assembly of the Bacillus subtilis spore coat, PLoS One, 9(9):e108560(1-16).
Press, 2007, Section 16.5, Support Vector Machines, Numerical Recipes: The Art of Scientific Computing (3rd Ed.), New York: Cambridge University (1262 pages).
Pritchard, 2004, The role of F-actin in hypo-osmotically induced cell volume change and calcium signaling in anulus fibrosus cells, Ann Bio med Eng, 32(1):103-11.
Radmacher, 2007, Studying the mechanics of cellular processes by atomic force microscopy, Methods Cell Biol, 83:347-72.
Ramanathan, 2015, Cdk1-dependent mitotic enrichment of cortical myosin II promotes cell rounding against confinement, Nat Cell Biol, 17(2):148-59.
Riedel, 2008, Lifeact: a versatile marker to visualize F-actin, Nat Methods, 5(7):605-7.
Rinke, 2014, Obtaining genomes from uncultivated environmental microorganisms using FACSbased single-cell genomics, Nat Protoc, 9(5):1038-48.

(56) References Cited

OTHER PUBLICATIONS

Rodrigues, 2015, Kinetochore-localized PP1-Sds22 couples chromosome segregation to polar relaxation, Nature, 524(7566):489-92, Suppl Info (18 pages).
Sader, 2010, Energy dissipation in microfluidic beam resonators: Dependence on mode number, J Appl Phys, 108(11):114507(1-14).
Sader, 2011, Energy dissipation in microfluidic beam resonators: Effect of Poisson's ratio, Phys Rev E Stat Nonlin Soft Matter Phys, 84(2 Pt 2):026304(1-15).
Scherrer, 1971, Macromolecular sieving by the dormant spore of Bacillus cereus, J Bacteriol, 108(2):868-73.
Scherrer, 1974, Porosity of the yeast cell wall and membrane, J Bacteriol, 118(2):534-40.
Scherrer, 1977, Density, porosity, and structure of dried cell walls isolated from Bacillus megaterium and *Saccharomyces cerevisiae*, J Bacteriol, 129(2):1162-4.
Sell, 2011, A digital PLL circuit for resonator sensors, Sensors and Actuators A, 172(1):69-74.
Simonyan, 2014, Very deep convolutional networks for large-scale image recognition, CoRR, abs/3409.1556, (14 pages).
Simpson, 2009, ABySS: A parallel assembler for short read sequence data, Genome Res., 19(6):1117-23.
Solla, 2000, Advances in Neural Information Processing Systems 12, MIT Press, pp. 512-518.
Son, 2012, Direct observation of mammalian cell growth and size regulation, Nat Methods, 9(9):910-2.
Son, 2015, Resonant microchannel volume and mass measurements show that suspended cells swell during mitosis, J Cell Biol, 211(4):757-63.
Steltenkamp, 2006, Membrane stiffness of animal cells challenged by osmotic stress, Small, 2(8-9):1016-20.
Stevens, 2016, Drug sensitivity of single cancer cells is predicted by changes in mass accumulation rate, Nat Biotechnol, 34(11):1161-1167.
Stewart, 2011, Hydrostatic pressure and the actomyosin cortex drive mitotic cell rounding, Nature, 469(7329):226-30, Supplementary Information (19 pages).
Swaminathan, 2011, Mechanical stiffness grades metastatic potential in patient tumor cells and in cancer cell lines, Cancer Res, 71(15):5075-80.
Szegedy, 2015, Going deeper with convolutions, in CVPR (12 pages).
Tang, 2017, High-throughput screening of rare metabolically active tumor cells in pleural effusion and peripheral blood of lung cancer patients, PNAS, 114(14):2544-2549.
Tseng, 2002, Micromechanical mapping of live cells by multiple-particle-tracking microrheology, Biophys J, 83(6):3162-76.
Wang, 1993, Mechanotransduction across the cell surface and through the cytoskeleton, Science, 260(5111):1124-7.
Wang, 2013, Acoustophoretic force-based compressibility measurement of cancer cells having different metastatic potential, Proc Mtgs Acoust, 19:045019(1-5).
Wang, 2015, Face Search at Scale: 80 Million Gallery, MSU Technical Report MSU-SCE-15-11 (14 pages).
Wang, 2016, Fast stiffness mapping of cells using high-bandwidth atomic force microscopy, ACS Nano, 10(1):257-64.
Warren, 2007, Assembling millions of short DNA sequences using SSAKE, Bioinformatics, 23:500-501.
Yang, 2016, A comprehensive strategy for the analysis of acoustic compressibility and optical de formability on single cells, Sci Rep, 6:23946(1-11).
Yeung, 1989, Cortical shell-liquid core model for passive flow of liquid-like spherical cells into micropipets, Biophys J, 56(1):139-49.
Zerbino, 2008, Velvet: Algorithms for de novo short read assembly using de Bruijn graphs, Genome Research 18(5):821-829.
Zlotek-Zlotkiewicz, 2015, Optical volume and mass measurements show that mammalian cells swell during mitosis, J Cell Biol, 211(4):765-74.
Cetin, Arif E, et al., "Determining therapeutic susceptibility in multiple myeloma by single-cell mass accumulation", Nature Communications, vol. 8, No. 1, Dec. 1, 2017 (Dec. 1, 2017), XP055899002, DOI: 10.1038/s41467-017-01593-2.
Kimmerling, Robert J, et al., "Linking single-cell measurements of mass, growth, rate, and gene expression", Genome Biology, vol. 19, No. 1, Dec. 1, 2018 (Dec. 1, 2018), XP055944647, DOI: 10.1186/s13059-018-1576-0.

\* cited by examiner

IDENTIFYING CANCER THERAPIES

CROSS-REFERENCE TO RELATED APPLICATIONS

This application claims the benefit of, and priority to, U.S. Provisional Patent Application No. 62/790,735, filed Jan. 10, 2019, the contents of which are incorporated by reference.

TECHNICAL FIELD

The disclosure relates to the identification of cancer therapies and functional feature measurements in cells.

BACKGROUND

Cancer represents a significant cost in both lives and healthcare dollars. While a complete cure is the ultimate goal, a more practical goal is to manage control of the patient's cancer (i.e., the cancer is still present but not spreading over time). Other positive outcomes include complete or partial remission where cancer has responded to a treatment and is either significantly reduced (partial remission) or undetectable via radiological imaging or histological examination (complete remission).

Unfortunately, remission and control can be fleeting and cancer often recurs or progresses after initially responding to treatment and maintenance therapies. Due the nature of cancer cells and tumors, drug targets can change through continued mutation and cancers can often develop resistance to previously effective therapies. Accordingly, individuals with previously controlled cancers or cancers in remission may face a real possibility of recurrence. When recurrence does occur, patients are left with few obvious options given that previously effective treatments no longer impact the cancer.

SUMMARY

The invention provides methods to identify treatments that are useful for treating cancer. Methods of the invention determine a match between types of cancer that affect only a small number of patients and drugs that are not typically considered for cancer treatment. Preferred methods include obtaining a biological sample containing cancer cells and identifying potential therapeutics based on information, such as cancer type, treatment history, demographic information, claims data, etc. Additional factors may include toxicology, efficacy, pharmacokinetics, side-effects, drug interactions, and cost. An in vitro assay is performed on the the obtained sample to assess the identified therapeutics. Preferably, the assay involves measuring a functional property of living cancer cells in response to exposure to the identified therapeutics. Results of the assay are then used to inform therapeutic choice. For example, where living cancer cells are known to accumulate mass, the assay can show drug efficacy when live cells from the sample show no mass accumulation upon treatment with the therapeutic.

The identification of therapeutics typically is performed in silico. The combination of patient history with therapeutic candidates and in vitro assay against living cancer cells provides the ability to rapidly identify treatments for otherwise difficult-to-treat cancers. The in vitro assay of live cancer cells from a patient expands the domain of personalized medicine beyond genomics and into the realm of functional cellular properties. In genomic personalized medicine, nucleic acid markers are a proxy for disease state. In methods of the invention, cell vitality is directly measured in vitro, and cell growth or mass accumulation provides a direct indication of a drug's effect on cancer cells. Due to the rapidity and economy of the in vitro functional assays of the invention, and the ability of those instruments to measure functional properties of isolated living cells, a new dimension of personalized medicine is brought to cancer patients. Drugs, or drug combinations, that would otherwise have been overlooked, or would have been cost-prohibitive for a population at large, can be tested on and used to treat individual patients or patients with cancers of a certain type, or small categories of cancers that are otherwise difficult to treat.

The invention uses systems and methods for identifying effective cancer therapies. In silico analysis of patient data combined with functional measurements of cancer cells allow for the identification of a best match between certain cancers or cancer types and cancer treatments (e.g., drugs or combinations of drugs). The systems and methods described herein have particular use for identifying treatments for cancers of certain types or in certain circumstances, such as cancers that recur after an earlier treatment may no longer provide positive results. A database including therapeutic, patient, and outcome information can be queried to determine a subset of possible effective therapies based on certain criteria and past results and patterns in the data. The database can be updated with each new patient's information and outcome. Upon identifying a subset of possible therapies from the in silico analysis, systems and methods of the invention offer rapid, inexpensive assays for testing the effectiveness of the identified therapies (or combinations thereof) on live cancer cells isolated from the patient. The availability of such assays provides for the testing of a large number and wide variety of therapies, and combinations of the therapies, in order to identify an effective treatment for a certain cancer.

Accordingly, less obvious treatment options can be explored and new therapies or new applications for existing therapies may be identified. Results of the efficacy assays can be fed back into the database along with information about the patient and their cancer cells as well as eventual treatment outcomes for the patient to refine the in silico analysis for future queries.

Database information used in the in silico analysis can include drug information such as toxicology, past efficacy, pharmacokinetics, and cost. Many features can be tied to specific patients (with associated patient and outcome information) or may be determined generally or through statistical analysis. Patient information may include, for example, genetic information, past treatments, age, gender, medical history, family history, and health measurements (e.g., weight, height, body mass index, blood pressure, cholesterol, and blood sugar). Outcomes with selected treatments can be tracked and linked to the above patient and drug information to build a more robust database and identify new links between patient or drug features and expected outcomes Embodiments of the invention discover correlations among drugs and cancers or cancer types through the use of machine learning analysis. Machine learning analysis can include for example, a random forest, a support vector machine (SVM), or a boosting algorithm (e.g., adaptive boosting (AdaBoost), gradient boost method (GSM), or extreme gradient boost methods (XGBoost)), or neural networks such as H2O. In certain embodiments features such as drug cost, side-effects, drug interactions, patient compliance and availability may be withheld from the machine learning analysis used to identify correlations between drug, patient, and cancer characteristics and treatment outcomes. Those features may be then included in subsequent application of the learned correlations in in silico analysis determinations of recommended treatments for patient-specific efficacy trials. While considerations such as cost and availability may not impact drug effectiveness they can be important considerations when determining a practical treatment for a given patient.

Assays may provide functional measurements of living cells such as mass and mass accumulation. In certain embodiments measurements can be determined using a suspended microchannel resonator. Suspended microchannel resonators are described in Cermak, 2016, High-throughput measurement of single-cell growth rates using serial microfluidic mass sensor arrays, Nat Biotechnol, 34(10): 1052-1059, incorporated by reference. By measuring functional features of living cells in the presence of various therapeutics, the effects of those therapeutics on the functional features can be observed and used to identify recommended treatments and to compare the efficacy of different possible treatments.

By analyzing changes in measurements such as mass accumulation of the patient's living cancer cells in the presence of various therapeutics, methods of the invention can be used to assess their efficacy in treating a specific patient's cancer. Determining therapeutic susceptibility of cancer cells through monitoring of mass-accumulation using suspended microchannel resonators may be performed using techniques described in Cetin, 2017, Determining therapeutic susceptibility in multiple myeloma by single-cell mass accumulation, Nat Com 8:1613, incorporated by reference. Because cancers reflect a patient's personal genomics and involve rapid mutational development, each patient's cancer is unique and can respond differently to different treatments. Accordingly, direct efficacy analysis against the patient's own cancer cells provides useful insight in identifying, prescribing, and developing successful therapies.

An advantage of functional measurements using methods of the invention on living cells is that the cell is maintained for subsequent analysis. Accordingly, in addition to functional measurements such as mass accumulation measured by suspended microchannel resonators, secondary assays such as molecular analyses of cancer proteins or nucleic acids can be conducted to provide more detail regarding the patient's cancer. Exemplary assays include gene expression, sequencing analysis, For example, additional assays may include genome sequencing, single cell transcriptomics, single cell proteomics, or single cell metabolomics. When using other, destructive assays, additional analyses may require additional samples that may be difficult to obtain, especially when invasive or painful biopsies are required or where sample is limited (e.g., an excised skin lesion). Accordingly, the ability of the functional measurement techniques described herein to leave intact cells for subsequent analysis allows for more detailed characterization of a patient's cancer in an efficient, less expensive, and less invasive manner.

Additionally, systems of the invention, especially when using suspended microchannel resonator analysis, can incorporate the additional analyses into a single microfluidic system. Microfluidic sequencing, flow cytometry, microarrays, and other analysis systems are well known and can be integrated into a microfluidic system downstream of the suspended microchannel resonator array in a single or modular system with exchangeable components depending on the secondary analysis to be performed.

Systems and methods of the invention can be performed on a variety of patient samples including cancer cells isolated from patient bodily fluids (e.g., mucous, blood, plasma, serum, serum derivatives, bile, blood, maternal blood, phlegm, saliva, sputum, sweat, amniotic fluid, menstrual fluid, mammary fluid, follicular fluid of the ovary, fallopian tube fluid, peritoneal fluid, urine, semen, and cerebrospinal fluid (CSF), such as lumbar or ventricular CS) or tissue samples (e.g., fine need biopsies). Where tissue samples are obtained, systems and methods of the invention may include tissue disaggregation steps in order to isolate single cells for functional analysis and other assays described herein.

Aspects of the invention include a method for selecting a cancer treatment. A biological sample containing cancer cells is obtained from a patient and a therapeutic that meets predetermined criteria relating to toxicology, efficacy, pharmacokinetics, or cost is determined. An in vitro assay is performed to determine efficacy of the identified therapeutic and, if the efficacy is above a threshold, the identified therapeutic is selected for treating the patient's cancer. The biological sample can be from a patient having received a prior therapy for cancer.

The predetermined criteria can include the prior therapy the patient has received. In certain embodiments, the in vitro assay measures a functional feature of live cells of the biological sample. The functional feature can include change in mass of the live cancer cells. The change in mass may be measured using at least one suspended microchannel resonator.

Methods of the invention may also include isolating individual, live cells, from the biological sample before performing the in vitro assay. The biological sample may include a tissue sample and the tissue sample can be a biopsy sample. The biopsy sample may be obtained by fine needle biopsy and comprises less than 50,000 cancer cells.

In certain embodiments, the one or more of the live cells can be collected after performing the in vitro assay. The collected cells can then be analyzed for a cancer biomarker. The analyzing step can include extracting nucleic acid or protein from the collected one or more cells and performing a biomarker assay on the extracted nucleic acid or protein to identify a cancer biomarker. The identifying step can include categorizing treatments with respect to cancer type. In certain embodiments, methods of the invention may include recording, in a database, one or more of the functional feature measurement, the therapeutic, the predetermined criteria, patient data, and patient response to the therapeutic. Methods can include updating one or more of the group consisting of the toxicology, the efficacy, the pharmacokinetics, and the cost of the therapeutic with information from the database. The in vitro assay may be performed within about 6, 24, or 48 hours after obtaining the biological sample in various embodiments.

The systems and methods described herein may include identifying new compounds or new uses for previously known compounds in treating developing cancers. Accordingly methods of the invention may include pricing or re-pricing therapeutics based on newly found or revised efficacies identified using the systems and methods described herein.

DETAILED DESCRIPTION

Systems and methods of the invention provide tools for determining a subset of possible therapies that may be effective in treating a cancer. Methods of the disclosure involve testing efficacy on living cancer cells using a cost-effective assay of functional properties of those cells. The assay of functional properties may include measuring mass or mass change using a suspended resonating cantilever. Assays described herein include measuring mass accumulation in living cancer cells from obtained from a patient in the presence of various therapeutics. Because the assays are carried out on living cells, subsequent analyses can be made on those same living cells to provide additional information (e.g., genomic sequencing) from those living cells without the need for additional sample.

Patient, drug, and cancer information can be held, updated, and analyzed in a database along with recorded outcomes. Data can be analyzed using machine learning to identify correlations between various patient, cancer, and drug characteristics and expected outcomes and drug efficacies. As discussed in more detail below, systems and methods of the invention allow for the tracking and identification of new or repurposed cancer therapies with exquisitely personal efficacy determinations.

Figure 1:
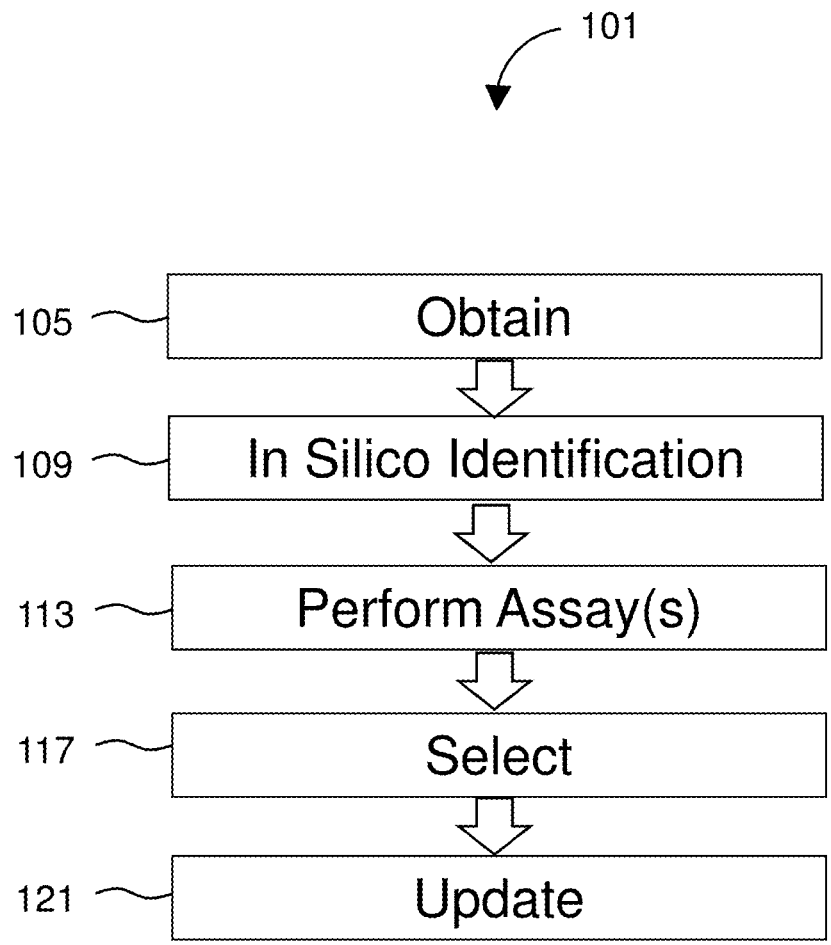
FIG. 1 diagrams a method for identifying cancer therapies.

FIG. 1 illustrates an exemplary method 101 for identifying cancer treatments. Cancer describes several diseases characterized by abnormal cell growth capable of spreading to other parts of the body. Types of cancer are characterized by the cells from which they originate. Cancer types include carcinomas such as breast, prostate, lung, pancreatic, and colon cancers that arise from epithelial cells. Sarcomas are derived from connective tissue (e.g., bone, cartilage, fat, or nerve cells). Lymphoma and leukemia arise from hematopoietic cells and are found in the lymph nodes and blood of afflicted patients. Cancer of plasma cells (myeloma) is another cancer found in blood. Germ cell cancers derived from pluripotent cells and blastomas from precursor cells or embryonic tissue are other types of cancer. Systems and methods of the invention relate to identifying treatments for any of the above cancer types including both those readily detectable in body fluids (e.g., lymphoma, leukemia, or multiple myeloma) as well as solid tumors (e.g., carcinomas or sarcomas).

In various embodiments, treatments or therapeutics are examined (in silico and/or in vitro), selected, and administered. Cancer treatments can include surgical intervention to remove solid tumors as well as non-surgical treatments. Systems and methods of the invention can evaluate the effectiveness of various non-surgical therapeutics or treatments on live cancer cells. Non-surgical treatments include, for example, chemotherapy, radiation, targeted therapies, immunotherapy, hormonal therapies, or any combination thereof. Chemotherapies involve cytotoxic drugs that preferentially target rapidly dividing cells. For example Docetaxel, used to treat breast cancer, head and neck cancer, stomach cancer, prostate cancer and non-small-cell lung cancer, suppresses microtubule dynamic assembly and disassembly in dividing cells, thereby inhibiting mitotic cell division and preventing cancer cells from proliferating. Radiation therapy uses focused ionizing radiation to damage the DNA of cancer cells and lead to cell death.

Targeted therapies include the use of agents that interfere with specific targeted molecules needed for carcinogenesis and tumor growth. Targeted therapies contrast with chemotherapies in that they specifically target cancer cells as opposed to rapidly-dividing cells generally. Targeted therapies include small molecules (e.g., Imatinib, Gefitinib, Erlotinib, Sorafenib, Sunitinib, Dasatinib, Lapatinib, Nilotinib, Bortezomib, tamoxifen, Janus kinase inhibitors, ALK inhibitors, Bcl-2 inhibitors, PARP inhibitors, PI3K inhibitors, Apatinib, AN-152, Braf inhibitors, serine/threonine kinase inhibitors, MEK inhibitors, CDK inhibitors, Hsp90 inhibitors, salinomycin, and VAL-083 (dianhydrogalactitol)), small molecule drug conjugates such as vintafolide, and monoclonal antibodies and antibody-drug conjugates targeting cancer-specific proteins and including Rituximab, Trastuzumab, Alemtuzumab, Cetuximab, Panitumumab, and Ipilimumab.

Cancer immunotherapy or immune-oncology is a category of treatments relying on the artificial stimulation of the patient's immune system to target and inhibit or kill cancer cells in the patient's body. Immunotherapies can be passive or active. Passive immunotherapies include targeting cell surface receptors and inducing antibody-dependent cell-mediated cytotoxicity. Active immunotherapies involve isolating existing or engineering new tumor-specific immune cells, culturing those immune cells, and introducing them into the body to target and destroy the patient's cancer. Immune cells used in such therapies include natural killer (NK) cells, lymphokine-activated killer cells, cytotoxic T cells and dendritic cells.

Chimeric antigen receptor T cell (CAR-T) therapy is an active immunotherapy. T cells are harvested from a patient and genetically altered to add a chimeric antigen receptor that specifically recognizes cancer cells and then infused into the patient to attack their tumors.

Checkpoint inhibitor therapy is a form of passive immunotherapy that targets regulators in the immune system to block certain inhibitory checkpoints. Inhibitory checkpoints can be upregulated in certain cancers to inhibit T cell attacks and, therefore, blocking them can allow a patient's own immune system to recognize and destroy cancer cells. Checkpoint inhibitors include ipilimumab, nivolumab, pembrolizumab, and atezolizumab. Certain types of breast and prostate cancers produce hormone-sensitive tumors in which hormone therapies such as blocking estrogen or testosterone can inhibit tumor growth.

Any of the above treatments, above or in combination, targeting cancer cells themselves, can be evaluated using systems and methods of the invention by exposing living cancer cells isolated from a patient sample to the therapeutic compound or treatment and observing any changes in functional measurements such as mass accumulation.

FIG. 1 shows steps of a method 101. The method 101 includes obtaining 105 one or more cancer cells isolated from a sample of a patient for such analyses. One or more live cells are isolated from a biological sample of a patient known to have, or suspected of having, cancer. A biological sample may include a human tissue or bodily fluid and may be collected in any clinically acceptable manner. A tissue is a mass of connected cells and/or extracellular matrix material, e.g. skin tissue, hair, nails, nasal passage tissue, CNS tissue, neural tissue, eye tissue, liver tissue, kidney tissue, placental tissue, mammary gland tissue, placental tissue, mammary gland tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, blood, maternal blood, phlegm, saliva, sputum, sweat, amniotic fluid, menstrual fluid, mammary fluid, follicular fluid of the ovary, fallopian tube fluid, peritoneal fluid, urine, semen, and cerebrospinal fluid (CSF), such as lumbar or ventricular CS. A sample also may be media containing cells or biological material. A sample may also be a blood clot, for example, a blood clot that has been obtained from whole blood after the serum has been removed. In certain embodiments, the sample is blood, saliva, or semen collected from the subject.

Examples of biopsies that may provide cells for analysis using systems and methods described herein can include, needle biopsy, bone biopsy, bone marrow biopsy, liver biopsy, kidney biopsy, aspiration biopsy, prostate biopsy, skin biopsy, or surgical biopsy. Systems and methods of the invention should be performed using living cells. Accordingly, cells should be preserved in culture media or otherwise stored in a manner to minimize cell death. In order to facilitate a living sample, systems and methods of the invention can be applied to samples within less than about 1 hour, 6 hours, 12 hours, 24 hours, 36 hours, or 48 hours of obtaining the sample.

Samples can be obtained by excising tissue or cells from a patient through, for example, a blood draw or biopsy. In certain embodiments, obtaining 105 a sample may include receiving a sample at, for example, a remote laboratory. The sample may have been taken by a medical professional at a hospital or other medical center and packaged and transported to the laboratory for analysis. Obtaining the sample may include opening the packaged sample before conducting an analysis thereof.

The isolation of the one or more live cells from the biological sample may be performed via any known isolation techniques and methods for maintaining a viable collection of cells, which may include one or cancer and/or cancer-related immune cells (e.g., lymphocytes includes T-cells and/or B-cells). For example, if the sample is a tissue sample from a tumor or growth suspected of being cancerous, the tissue sample may undergo any known cell isolation, separation, or dissociation techniques which may involve physical methods (i.e., use of mechanical force to break apart cellular adhesions) and/or reagent-based methods (i.e., use of fluid mediums to break apart cellular adhesions). For example, in one embodiment, a tissue sample (i.e., a fine needle aspirate from a tumor) may be disaggregated to produce a suspension of individual live cells to allow for analysis of cells independently. Cells may be isolated from patient bodily fluids or tissue samples. Where tissue samples are obtained, systems and methods of the invention may include tissue disaggregation steps in order to isolate single cells for functional analysis and other assays described herein. The extracellular matrix of tissue samples must be broken down to recover single cells. Many procedures for dissociating solid tumors are known as described, for example, in Robert Cunningham, 1999, Tissue Disaggregation, Methods in Molecular Biology, 115: 257-60, incorporated herein by reference. Disaggregation methods include one or more mechanical, enzymatic, or chemical manipulations. The tissue sample may undergo initial disaggregation by way of application of a physical force alone to break the tissue sample into smaller pieces, at which point the sample may be exposed to proteolytic enzymes that digest cellular adhesion molecules and/or the underlying extracellular matrix to thereby provide single cells within a suspension. It should be noted that the reagents selected for assisting in the disaggregating step should keep the cells intact and not kill the cells.

Other methods currently used for single cell isolation include, but are not limited to, serial dilution, micromanipulation, laser capture microdissection, FACS, microfluidics, Dielectrophoretic digital sorting, manual picking, and Raman tweezers. Manual single cell picking is a method is where cells in a suspension are viewed under a microscope, and individually picked using a micropipette, while Raman tweezers is a technique where Raman spectroscopy is combined with optical tweezers, which uses a laser beam to trap, and manipulate cells. Dielectrophoretic (DEP) digital sorting method utilizes a semiconductor controlled array of electrodes in a microfluidic chip to trap single cells in DEP cages, where cell identification is ensured by the combination of fluorescent markers with image observation and delivery is ensured by the semiconductor controlled motion of DEP cages in the flow cell.

The method 101 further includes identifying 109, in silico, one or more therapeutics that meet predetermined criteria relating to toxicology, efficacy, pharmacokinetics, side-effects, drug interactions, patient compliance, or cost. The predetermined criteria may be preset for general patients or classes of patients or may be patient-specific. For example, patients in a certain age group may have lower thresholds for toxicology and patients in a certain economic group (or without insurance coverage) may have a lower tolerance for cost. In such cases, patient information may be supplied to determine the thresholds. Patient information may include genetic information, past treatments, age, gender, medical history, family history, and health measurements (e.g., weight, height, body mass index, blood pressure, cholesterol, and blood sugar), race, income, insurance status and ability to pay, environmental or geographic information and history (e.g., place of birth and historic and current places of residence). Patient information may be obtained directly from the patient or individuals associated with the patient through, for example, a questionnaire or an interview. The information can also be obtained from a medical professional after consultation with the patient. In certain embodiments, patient information may be obtained, along with a patient sample, by a medical professional and transmitted (physically or electronically) to a remote laboratory where the in silico analysis can be conducted and the sample can be processed.

Once the predetermined thresholds are determined and entered, the in silico analysis can proceed. The analysis can access a database of drug information to identify all of the therapies that meet each criterion. For example, a patient with compromised liver function may be identified to the system. Accordingly, the database will be searched for drugs and therapies that do not involve prodrugs that require liver processing. The results will be examined based on the remaining criteria before a set of results consisting of therapeutics meeting each of the criteria thresholds is determined. The in silico analysis can result in a list of potential therapies being output (e.g., on a display or printed report).

Criteria such as toxicology, efficacy, side-effects, drug interactions, and patient compliance may be analyzed based on specific patient data using correlations identified through machine learning analysis as described below. Accordingly, patient information and any known cancer information may be provided for in silico analysis to predict toxicology, efficacy, side-effects, drug interactions, or patient compliance for a given therapy based on machine-learning-identified links between those parameters and the received patient or cancer information. The predicted toxicology, efficacy, side-effects, drug interactions, or patient compliance for a given therapy and patient can then be compared to the predetermined criteria to identify 109 a subset of therapeutics for further analysis. In such embodiments known patient or cancer information can include previously obtained genomic or proteomic data relating to the patient or their cancer in addition to the characteristics described below.

After identifying 109 therapeutics meeting the predetermined criteria, the cancer cells can be assayed 113 to determine efficacy of the identified therapeutics. As discussed below, assay(s) can include measuring a functional cancer biomarker in the one or more live cells. For example, in one embodiment, the functional cancer biomarker includes mass and/or mass change of the one or more live cells in the presence of one or more of the identified therapeutics. In some embodiments, as will be described in greater detail herein, the first assay involves loading individual live cells into a measurement instrument and flowing the live cells through the measurement instrument. The measurement instrument may generally include a microfluidic platform capable of direct measurement of single-cell mass and growth rate. Upon flowing the live cells through the measurement instrument, a functional cancer biomarker in the one or more live cells is obtained, the functional cancer biomarker including mass or mass accumulation rate (MAR). The live cells remaining in a living state upon passing through the measurement instrument, such that they are accessible for one or more additional live cell assays downstream from the first assay. Additional assays can be performed on the cells in combination with the functional measurement and can include genome sequencing, single cell transcriptomics, single cell proteomics, and single cell metabolomics.

The method 101 further includes selecting 117 one or more of the identified therapeutics for treating the patient's cancer where the determined efficacy is above a certain threshold. In certain embodiments, the therapy may be selected by comparing the determined efficacies of all measured therapeutics that were identified in step 109 and selecting the most effective. The method 101 can further include updating 121 the database with the results of the efficacy assay along with the patient's data and any cancer data obtained through additional assays for further machine learning analysis. Real world outcomes for the patient including responsiveness to the treatment can also be tracked and fed back into the database for refined database queries or for machine learning analysis. As more information is obtained and analyzed, the patterns identified by a machine learning algorithm can improve in accuracy.

Any machine learning algorithm may be used for the systems and methods described herein including, for example, a random forest, a support vector machine (SVM), or a boosting algorithm (e.g., adaptive boosting (AdaBoost), gradient boost method (GSM), or extreme gradient boost methods (XGBoost)), or neural networks such as H2O. Machine learning algorithms generally are of one of the following types: (1) bagging, (2) boosting, or (3) stacking. In bagging, multiple prediction models (generally of the same type) are constructed from subsets of classification data (classes and features) and then combined into a single classifier. Random Forest classifiers are of this type. In boosting, an initial prediction model is iteratively improved by examining prediction errors. Adaboost.M1 and eXtreme Gradient Boosting are of this type. In stacking models, multiple prediction models (generally of different types) are combined to form the final classifier. These methods are called ensemble methods. The fundamental or starting methods in the ensemble methods are often decision trees. Decision trees are non-parametric supervised learning methods that use simple decision rules to infer the classification from the features in the data. They have some advantages in that they are simple to understand and can be visualized as a tree starting at the root (usually a single node) and repeatedly branch to the leaves (multiple nodes) that are associated with the classification.

Random forests use decision tree learning, where a model is built that predicts the value of a target variable based on several input variables. Decision trees can generally be divided into two types. In classification trees, target variables take a finite set of values, or classes, whereas in regression trees, the target variable can take continuous values, such as real numbers. Examples of decision tree learning include classification trees, regression trees, boosted trees, bootstrap aggregated trees, random forests, and rotation forests. In decision trees, decisions are made sequentially at a series of nodes, which correspond to input variables. Random forests include multiple decision trees to improve the accuracy of predictions. See Breiman, L. Random Forests, Machine Learning 45:5-32 (2001), incorporated herein by reference. In random forests, bootstrap aggregating or bagging is used to average predictions by multiple trees that are given different sets of training data. In addition, a random subset of features is selected at each split in the learning process, which reduces spurious correlations that can results from the presence of individual features that are strong predictors for the response variable.

SVMs can be used for classification and regression. When used for classification of new data into one of two categories, such as having a disease or not having a disease, a SVM creates a hyperplane in multidimensional space that separates data points into one category or the other. Although the original problem may be expressed in terms that require only finite dimensional space, linear separation of data between categories may not be possible in finite dimensional space. Consequently, multidimensional space is selected to allow construction of hyperplanes that afford clean separation of data points. See Press, W. H. et al., Section 16.5. Support Vector Machines. Numerical Recipes: The Art of Scientific Computing (3rd ed.). New York: Cambridge University (2007), incorporated herein by reference. SVMs can also be used in support vector clustering. See Ben-Hur, A., et al., (2001), Support Vector Clustering, Journal of Machine Learning Research, 2:125-137.

Boosting algorithms are machine learning ensemble meta-algorithms for reducing bias and variance. Boosting is focused on turning weak learners into strong learners where a weak learner is defined to be a classifier which is only slightly correlated with the true classification while a strong learner is a classifier that is well-correlated with the true classification. Boosting algorithms consist of iteratively learning weak classifiers with respect to a distribution and adding them to a final strong classifier. The added classifiers are typically weighted in based on their accuracy. Boosting algorithms include AdaBoost, gradient boosting, and XGBoost. Freund, Yoav; Schapire, Robert E (1997). "A decision-theoretic generalization of on-line learning and an application to boosting". Journal of Computer and System Sciences. 55: 119; S. A. Solla and T. K. Leen and K. Müller. Advances in Neural Information Processing Systems 12. MIT Press. pp. 512-518; Tianqi Chen and Carlos Guestrin. XGBoost: A Scalable Tree Boosting System. In 22nd SIGKDD Conference on Knowledge Discovery and Data Mining, 2016; the contents of each of which are incorporated herein by reference.

Machine learning algorithms can be trained on data sets useful for the intended purpose of the machine analysis. For example, to train for machine analysis of cancer cell features and patient data, a machine learning algorithm can be provided with a training data set including patient information, therapeutic information, cancer features, and associated outcomes for specific patient, therapeutic, and cancer combinations. The algorithm can then identify common patterns in the data that are indicative of an expected outcome. A particular advantage of machine learning algorithms is the ability to identify patterns that cannot be easily perceived by human analysis.

Considerations such as cost and availability of a given therapeutic may not impact drug effectiveness and, accordingly, may be omitted from machine learning analysis used to identify correlations between drug, patient, and cancer characteristics and treatment outcomes. Such considerations, as well as side-effects, drug interactions, and patient compliance can, however, be important considerations when determining a practical treatment for a given patient. Accordingly, that data may be included in subsequent application of the learned correlations in the in silico analysis determinations of recommended treatments for patient-specific efficacy trials.

Therapeutic information may include cost of the treatment, toxicology, pharmacokinetics, side effects, patient compliance, availability, drug interactions, and past efficacy. Many features can be tied to specific patients (with associated patient and outcome information) or may be determined generally or through statistical analysis. Patient information may include, for example, genetic information, past treatments, age, gender, medical history, family history, and health measurements (e.g., weight, height, body mass index, blood pressure, cholesterol, and blood sugar). Cancer information may include functional measurements and other assay-derived characteristics of the cancer cell and tissue samples as described below. Categories may overlap, for example, patient and drug information may both include a patient's past responsiveness to a particular drug. Outcomes may include, for example, complete or partial remission, a number of years lived after treatment, or a slowed disease progression. Outcomes with selected treatments can be tracked and linked to the above patient and drug information to build a more robust database and identify new links between patient or drug features and expected outcomes.

Figure 2:
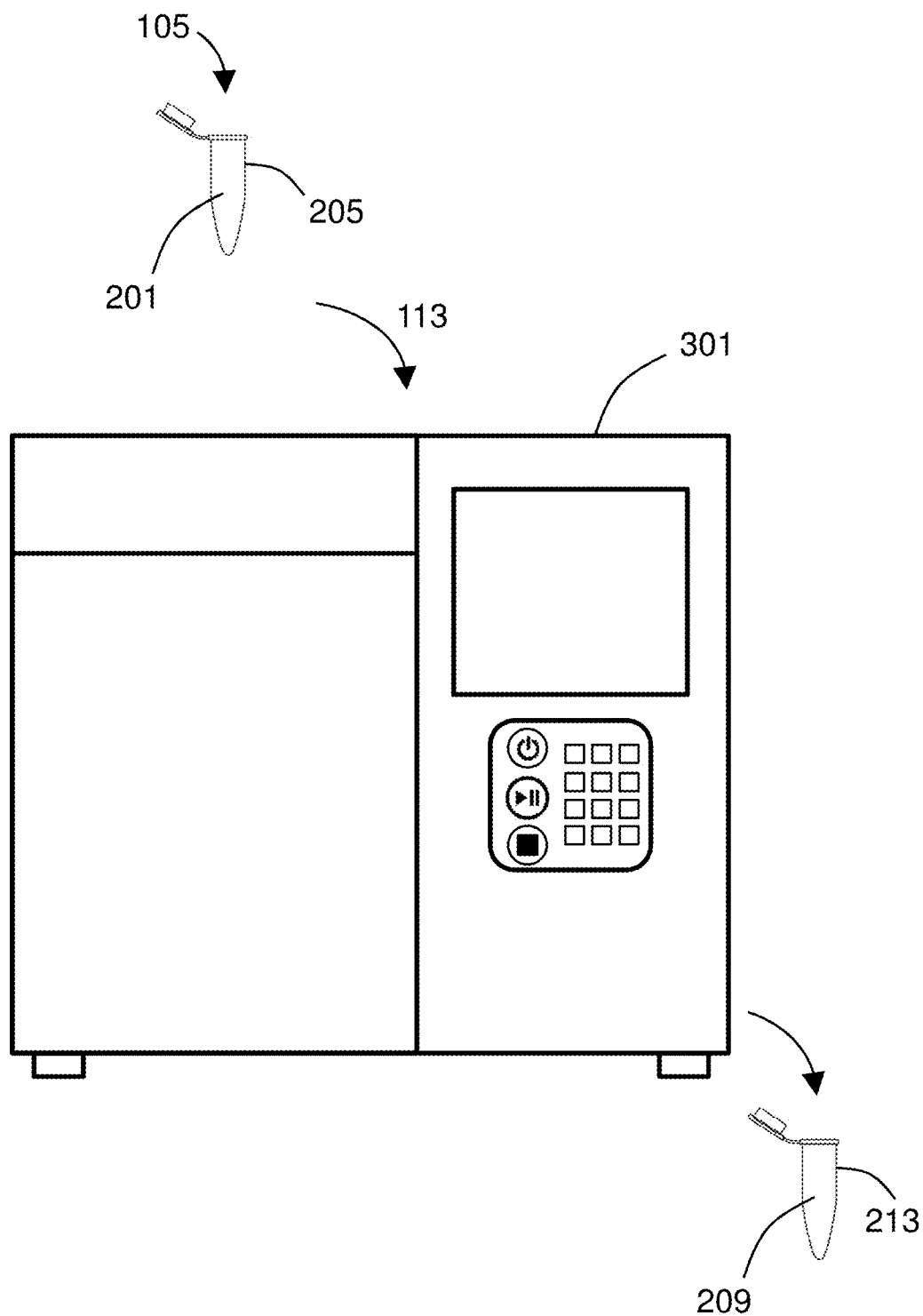
FIG. 2 shows loading live cells into a measurement instrument.

FIG. 2 shows a sample 201 provided within a suitable container 205, wherein the sample 201 includes one or more live cells including at least one of a cancer cell and a cancer-related immune cell obtained 105 from a patient known to have, or suspected of having, cancer. For example, in some embodiments, samples may be collected and stored in their own container, such as a centrifuge tube such as the 1.5 mL micro-centrifuge tube sold under the trademark EPPENDORF FLEX-TUBES by Eppendorf, Inc. (Enfield, CT). Live cells in the sample 201 are loaded into an instrument 301 capable of performing 113 the first assay on the one or more live cells. The instrument 301 measures a functional cancer biomarker in the one or more live cells, such as single-cell biophysical properties, including, but not limited to, mass, growth rate, and mass accumulation of an individual living cell. The initial assay may generally be performed with an instrument 301 comprising a suspended microchannel resonator (SMR). The SMR may be used to precisely measure biophysical properties, such as mass and mass changes, of a single cell flowing therethrough. The mass change may be mass accumulation rate (MAR). When used with cancer cells, those changes provide a functional, universal biomarker by which medical professionals (e.g., oncologists) may monitor the progression of a cancer and determine how cancer cells respond to therapies.

The SMR may comprise an exquisitely sensitive scale that measures small changes in mass of a single cell. When cancer cells respond to cancer drugs, the cells begin the process of dying by changing mass within hours. The SMR can detect this minor weight change. That speed and sensitivity allow the SMR to detect a cancer cell's response to a cancer drug while the cell is still living. Upon flowing the live cells through the SMR, a functional biomarker, such as mass or MAR, in the one or more live cells is obtained. MAR measurements characterize heterogeneity in cell growth across cancer cell lines. Individual live cells are able to pass through the SMR, wherein each cell is weighed multiple times over a defined interval. The SMR includes multiple sensors that are fluidically connected, such as in series, and separated by delay channels. Such a design enables a stream of cells to flow through the SMR such that different sensors can concurrently weigh flowing cells in the stream, revealing single-cell MARs. The SMR is configured to provide real-time, high-throughput monitoring of mass change for the cells flowing therethrough. Therefore, the biophysical properties, including mass and/or mass changes (e.g., MAR), of a single cell can be measured. Such data can be stored and used in subsequent analysis steps, as will be described in greater detail herein.

Upon passing through the instrument 301, single cells remain viable and can be isolated downstream from the instrument 301 and are available to undergo the subsequent assays. As shown, a sample 209 of the one or more live cells having undergone the first assay (i.e., passing through the instrument 301) are collected in a suitable container 213 and are then available to undergo a second assay.

Figure 3:
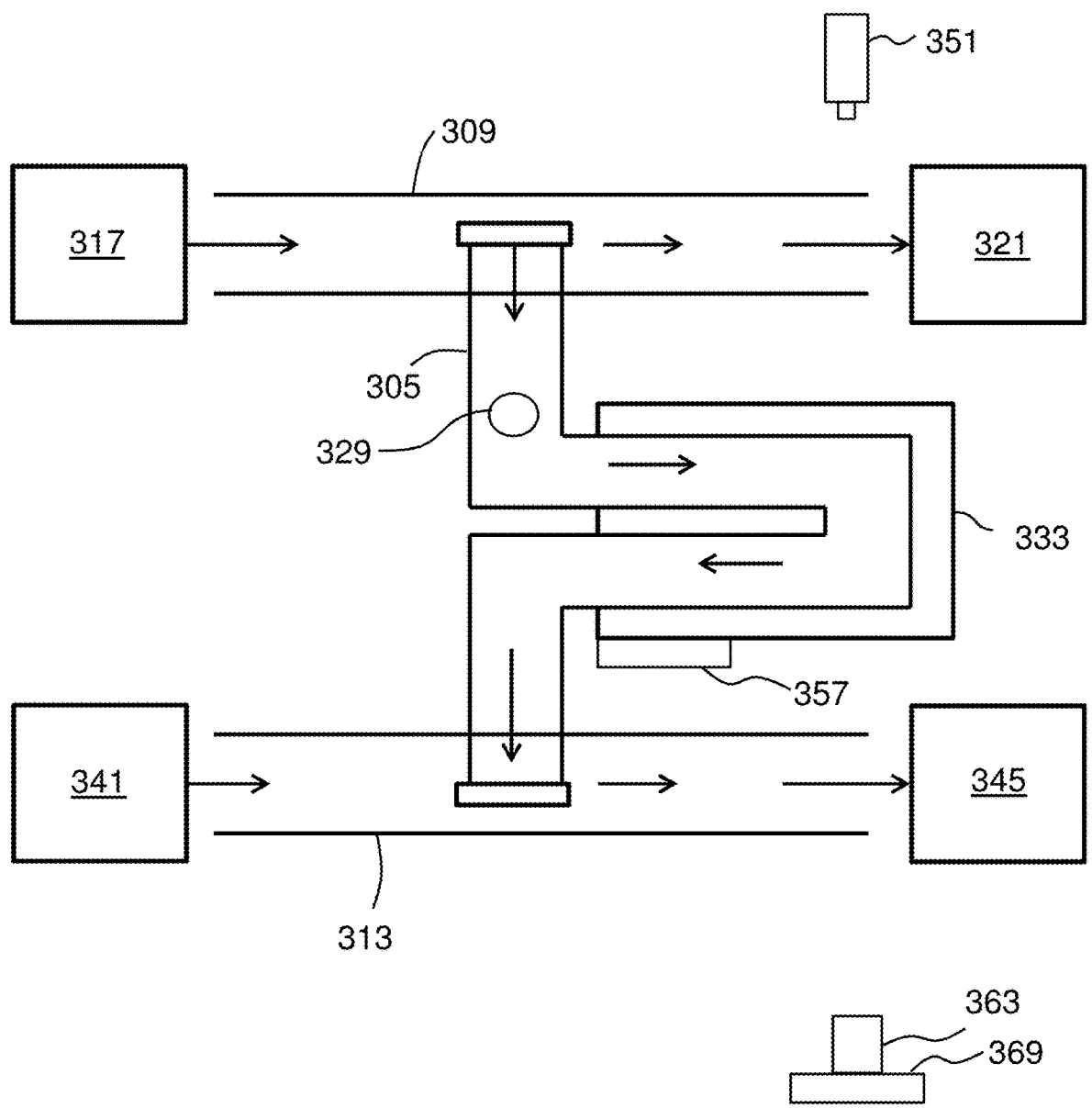
FIG. 3 shows a suspended microchannel resonator (SMR).

FIG. 3 shows a flow path through a suspended microchannel 305 of an SMR consistent with the present disclosure. As illustrated, the suspended microchannel 305 is suspended between an upper bypass channel 309 and a lower bypass channel 313. Having the two bypass channels allows for decreased flow resistance and accommodates the flow rate through the microchannel 305. Sample eluate 317 flows through the upper bypass channel 309, wherein a portion of the eluate 317 collects in the upper bypass channel waste reservoir 321. A portion of the eluate 317 including at least one live cell 329 flows through the suspended microchannel 305. The flow rate through the suspended microchannel 305 is determined by the pressure difference between its inlet and outlet. Since the flow cross section of the suspended microchannel is about 70 times smaller than that of the bypass channels, the linear flow rate can be much faster in the suspended microchannel than in the bypass channel, even though the pressure difference across the suspended microchannel is small. Therefore, at any given time, it is assumed that the SMR is measuring the eluate that is present at the inlet of the suspended microchannel. The sample includes a live cell or material with cell-like properties.

The cell 329 flows through the suspended microchannel 305. The suspended microchannel 305 extends through a cantilever 333 which sits between a light source 351 and a photodetector 363 connected to a chip 369 such as a field programmable gate array (FPGA). The cantilever is operated on by an actuator, or resonator 357. The resonator 357 may be a piezo-ceramic actuator seated underneath the cantilever 333 for actuation. The cell 329 flows from the upper bypass channel 309 to the inlet of the suspended microchannel 305, through the suspended microchannel 305, and to the outlet of the suspended microchannel 305 toward the lower bypass channel 313. A buffer 341 flows through the lower bypass channel towards a lower bypass channel collection reservoir 345. After the cell 329 is introduced to the lower bypass channel 313, the cell 329 is collected in the lower bypass collection reservoir 345.

Figure 4:
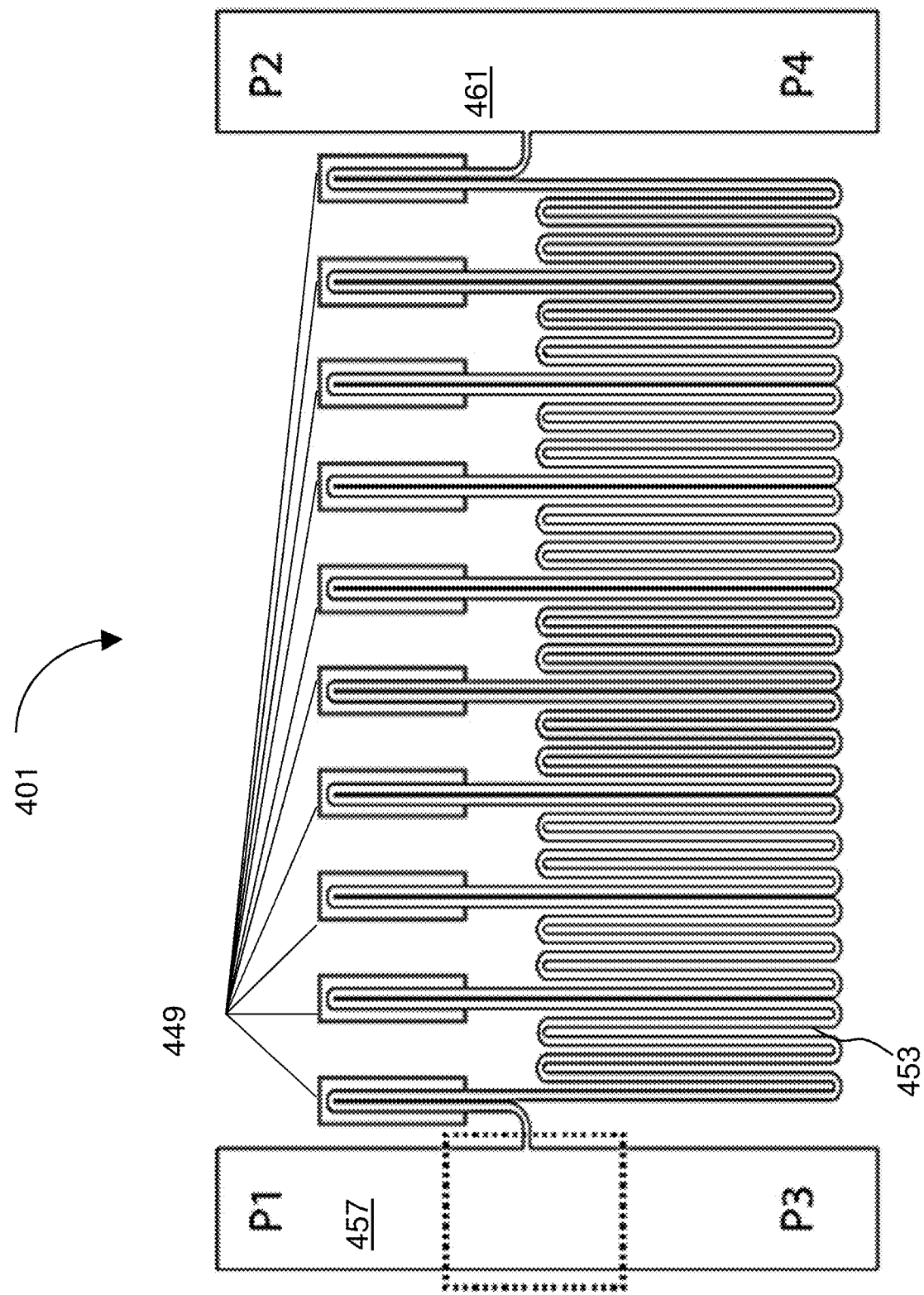
FIG. 4 shows a serial suspended microchannel resonator (sSMR) array.

In some embodiments, the instrument 301 comprises an array of SMRs with a fluidic channel passing therethrough. FIG. 4 shows a serial suspended microchannel resonator (sSMR) array 401, made up of an array of SMRs. An instrument that includes an sSMR array is useful for direct measurement of biophysical properties of single cells flowing therethrough. The sSMR includes a plurality of cantilevers 449 and a plurality of delay channels 453. Cells from the first bypass channel 457 through the cantilevers 449 and delay channels 453 to the second bypass channel 461. Pressure differences in the first bypass channel 457 are indicated by P1 and P2, and pressure differences in the second bypass channel 461 are indicated by P3 and P4.

Instruments 301 of the disclosure can make sensitive and precise measurements of mass or change in mass through the use of an sSMR array 401. The instruments use a structure such as a cantilever that contains a fluidic microchannel. Living cells are flowed through the structure, which is resonated and its frequency of resonation is measured. The frequency at which a structure resonates is dependent on its mass and by measuring the frequency of at which the cantilever resonates, the instrument can compute a mass, or change in mass, of a living cell in the fluidic microchannel. By flowing the isolated living cells from the tissue sample through such devices, one may observe the functions of those cells, such as whether they are growing and accumulating mass or not. The mass accumulation or rate of mass accumulation can be related to clinically important property such as the presence of cancer cells or the efficacy of a therapeutic on cancer cells.

Methods for measuring single-cell growth are based on resonating micromechanical structures. The methods exploit the fact that a micromechanical resonator's natural frequency depends on its mass. Adding cells to a resonator alters the resonator's mass and causes a measurable change in resonant frequency. Suspended microchannel resonators (SMRs) include a sealed microfluidic channel that runs through the interior of a cantilever resonator. The cantilever itself may be housed in an on-chip vacuum cavity, reducing damping and improving frequency (and thus mass) resolution. As a cell in suspension flows through the interior of the cantilever, it transiently changes the cantilever's resonant frequency in proportion to the cell's buoyant mass (the cell's mass minus the fluid mass it displaces). SMRs weigh single mammalian cells with a resolution of 0.05 pg (0.1% of a cell's buoyant mass) or better. The sSMR array 401 includes an array of SMRs fluidically connected in series and separated by delay channels 453 between each cantilever 349. The delay channels give the cell time to grow as it flows between cantilevers.

Devices may be fabricated as described in Lee, 2011, Suspended microchannel resonators, Lab Chip 11:645 and/or Burg, 2007, Weighing of biomolecules, Nature 446:1066-1069, both incorporated by reference. Large-channel devices (e.g., useful for PBMC measurements) may have cantilever interior channels of 15 by 20 μm in cross-section, and delay channels 20 by 30 μm in cross-section. Small-channel devices (useful for a wide variety of cell types) may have cantilever channels 3 by 5 μm in cross-section, and delay channels 4 by 15 μm in cross-section. The tips of the cantilevers in the array may be aligned so that a single line-shaped laser beam can be used for optical-lever readout. The cantilevers may be arrayed such that the shortest (and therefore most sensitive) cantilevers are at the ends of the array. Before use, the device may be cleaned with piranha (3:1 sulfuric acid to 50% hydrogen peroxide) and the channel walls may be passivated with polyethylene glycol (PEG) grafted onto poly-L-lysine. In some embodiments, a piezo-ceramic actuator seated underneath the device is used for actuation. The instrument 301 may include low-noise photodetector, Wheatstone bridge-based amplifier (for piezo-resistor readout), and high-current piezo-ceramic driver. To avoid the effects of optical interference between signals from different cantilevers (producing harmonics at the difference frequency), the instrument may include a low-coherence-length light source (675 nm super-luminescent diode, 7 nm full-width half maximum spectral width) as an optical lever. After the custom photodetector converts the optical signal to a voltage signal, that signal is fed into an FPGA board, in which an FPGA implements twelve parallel second-order phase-locked loops which each both demodulate and drive a single cantilever. The FPGA may operate on a 100 MHz clock with I/O provided via a high-speed AD/DA card operating 14-bit analog-to-digital and digital-to-analog converters at 100 MHz.

To operate all cantilevers in the array, the resonator array transfer function is first measured by sweeping the driving frequency and recording the amplitude and phase of the array response. Parameters for each phase-locked loop (PLL) are calculated such that each cantilever-PLL feedback loop has a 50 or 100 Hz FM-signal bandwidth. The phase-delay for each PLL may be adjusted to maximize the cantilever vibration amplitude. The FM-signal transfer function may be measured for each cantilever-PLL feedback loop to confirm sufficient measurement bandwidth (in case of errors in setting the parameters). That transfer function relates the measured cantilever-PLL oscillation frequency to a cantilever's time-dependent intrinsic resonant frequency. Frequency data for each cantilever are collected at 500 Hz, and may be transmitted from the FPGA to a computer. The device may be placed on a copper heat sink/source connected to a heated water bath, maintained at 37 degrees C. The sample is loaded into the device from vials pressurized under air or air with 5% $CO_2$ through 0.009 inch inner-diameter fluorinated ethylene propylene (FEP) tubing. The pressurized vials may be seated in a temperature-controlled sample-holder throughout the measurement. FEP tubing allows the device to be flushed with piranha solution for cleaning, as piranha will damage most non-fluorinated plastics. To measure a sample of cells, the device may initially flushed with filtered media, and then the sample may be flushed into one bypass channel. On large-channel devices, between one and two psi may be applied across the entire array, yielding flow rates on the order of 0.5 nL/s (the array's calculated fluidic resistance is approximately $3\times10^{16}$ Pa/(m3/s). For small-channel devices, 4-5 psi may be applied across the array, yielding flow rates around 0.1 nL/s. Additionally, every several minutes new sample may be flushed into the input bypass channel to prevent particles and cells from settling in the tubing and device. Between experiments, devices may be cleaned with filtered 10% bleach or piranha solution.

For the data analysis, the recorded frequency signals from each cantilever are rescaled by applying a rough correction for the different sensitivities of the cantilevers. Cantilevers differing in only their lengths should have mass sensitivities proportional to their resonant frequencies to the power three-halves. Therefore each frequency signal is divided by its carrier frequency to the power three-halves such that the signals are of similar magnitude. To detect peaks, the data are filtered with a low pass filter, followed by a nonlinear high pass filter (subtracting the results of a moving quantile filter from the data). Peak locations are found as local minima that occur below a user-defined threshold. After finding the peak locations, the peak heights may be estimated by fitting the surrounding baseline signal (to account for a possible slope in the baseline that was not rejected by the high pass filter), fitting the region surrounding the local minima with a fourth-order polynomial, and finding the maximum difference between the predicted baseline and the local minima polynomial fit. Identifying the peaks corresponding to calibration particles allows one to estimate the mass sensitivity for each cantilever, such that the modal mass for the particles is equal to the expected modal mass.

Peaks at different cantilevers that originate from the same cell are matched up to extract single-cell growth information. The serial SMR array and can measure live cells.

Certain embodiments include devices with piezo-resistors doped into the base of each cantilever, which are wired in parallel and their combined resistance measured via a Wheatstone bridge-based amplifier. The resulting deflection signal, which consists of the sum of k signals from the cantilever array, goes to an array of k phase-locked loops (PLLs) where each PLL locks to the unique resonant frequency of a single cantilever. Therefore there is a one to one pairing between cantilevers and PLLs. Each PLL determines its assigned cantilever's resonant frequency by demodulating its deflection signal and then generates a sinusoidal drive signal at that frequency. The drive signals from each PLL are then summed and used to drive a single piezo actuator positioned directly underneath the chip, completing the feedback loop. Each PLL is configured such that it will track its cantilever's resonant frequency with a bandwidth of 50 or 100 Hz. After acquiring the frequency signals for each cantilever, the signals are converted to mass units via each cantilever's sensitivity (Hz/pg), which is known precisely.

Various embodiments of SMR and sSMR instruments, as well as methods of use, include those instruments/devices manufactured by Innovative Micro Technology (Santa Barbara, CA) and described in U.S. Pat. Nos. 8,418,535 and 9,132,294, the contents of each of which are hereby incorporated by reference in their entirety.

Figure 5:
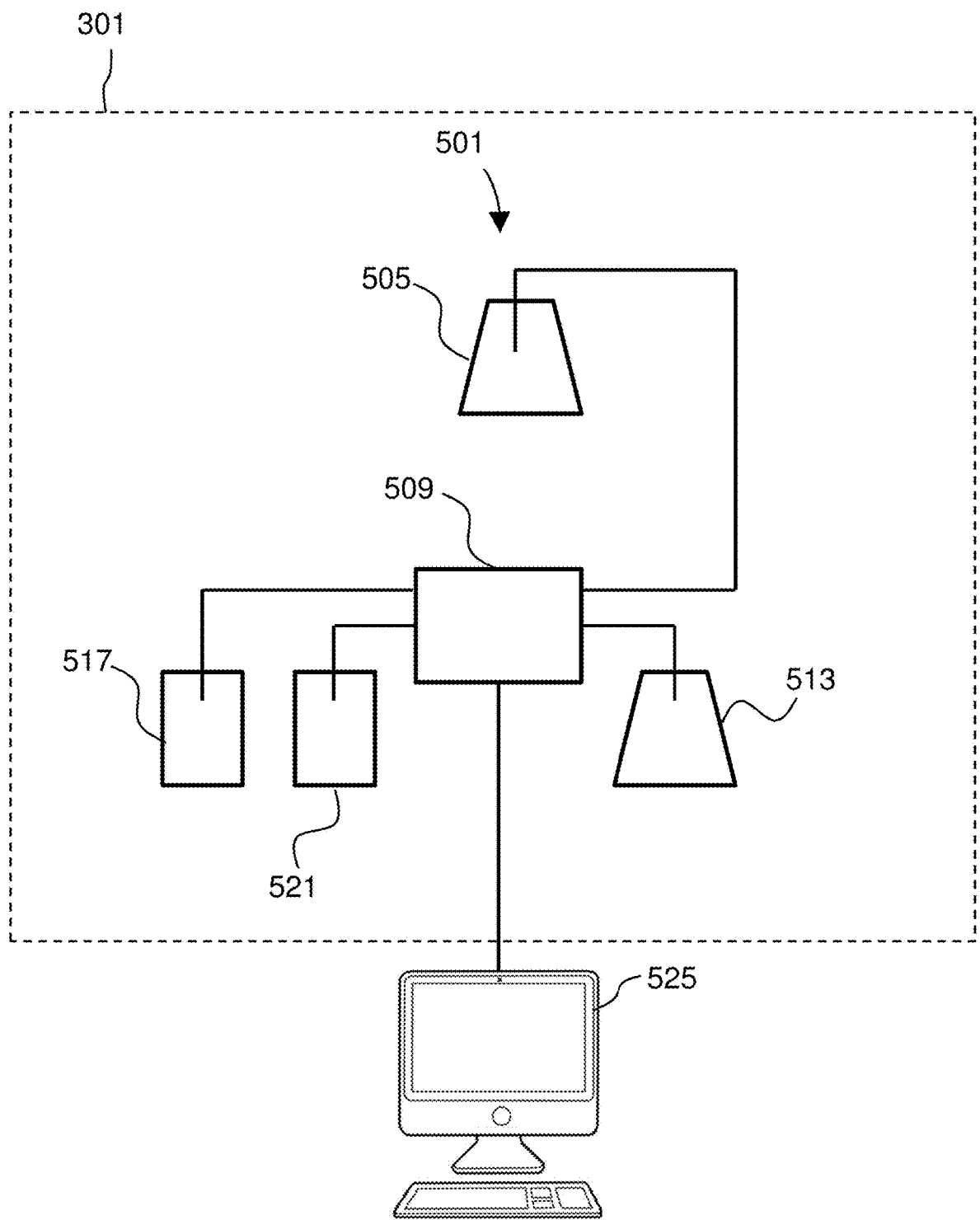
FIG. 5 is a block diagram of an exemplary SMR detection system of the disclosure.

FIG. 5 shows a schematic diagram of an SMR detection system 501. As shown, a sample 505 (i.e., one or more live cells provided in a fluid medium) may be introduced to the SMR 509 of an instrument 301. As shown, the sample 505 and a buffer solution 513 may be provided to the SMR. The system 501 further includes an upper bypass channel waste outlet/reservoir 517 and lower bypass channel waste outlet/reservoir 521. The SMR 509 is configured to measure a functional biomarker of one or more live cells 505 flowing therethrough, such as density or mass of the sample, and transmit such measurements to a computer 525 that is communicatively coupled to the SMR 509, specifically communicatively coupled to the instrument 301. The computer 525 may be used for analysis and reporting of results. In some embodiments, a system for the functional biomarker measurement instrument may include additional analytical techniques, as will be described in greater detail herein. The computer 525 may further comprise a server and storage. Any of the elements in the SMR detection system 501 may interoperate via a network. The SMR 409 may include its own on-board computer. The computer 525 may include one or more processors and memory as well as an input/output mechanism.

Upon passing through the instrument 301, namely the exemplary flow path of a suspended microchannel or the flow path of the sSMR array 401, the material 329, specifically the one or more live cells, remains viable and can be isolated downstream from the instrument 301 and are available to undergo the subsequent assays. The method further includes performing one or more additional assays on the live cells, either concurrently with the initial assay, or downstream from the first assay, to obtain further data associated with the live cells, such as additional functional data and/or genomic data.

It should be noted that methods of the disclosure may include performing one or more additional assays on the live cells, either concurrently with the first assay, or downstream from the first assay, to obtain further functional or genetic data. In some embodiments, the second assay is performed on the live cells having undergone the first assay, which allows for data obtained from the first and second assays to be linked at a single-cell level, as opposed to a population level.

The mass accumulation rates (or other functional measurement) of cells from the patient sample in the presence of various therapeutic compounds (e.g., a chemotherapeutic), after exposure to various treatments (e.g., radiation), or combinations thereof can be compared to one another to select a next treatment for the patient. The various therapeutic compounds having been determined by the above in silico analysis based on suitability and/or likelihood of success for the individual patient, a practical comparison of efficacy as determined by effect on mass accumulation rate can be used to select a single treatment or combination thereof from the original list of suitable compounds or therapies. In certain embodiments, the mass accumulation rates may be compared to a minimal threshold and all compounds or treatments having mass accumulation rates below that threshold may be include in a report as options for treatment. In some embodiments, the compound, treatment, or combination thereof that resulted in the lowest mass accumulation rate may be selected for prescription or administration to the patient.

As previously described, after functional measurement, the one or more live cells may undergo a second assay to obtain further functional or genetic data. It should be noted that methods of the disclosure include performing one or more additional assays on the live cells, either concurrently with the first assay, or downstream from the first assay, to obtain further functional or genetic data. The second assay is performed on the live cells having undergone the first assay, which allows for data obtained from the first and second assays to be linked at a single-cell level, as opposed to a population level.

In some embodiments, the second assay is selected from the group consisting of genome sequencing, single cell transcriptomics, single cell proteomics, and single cell metabolomics. Genome sequencing is generally the process of determining the order of nucleotides in DNA. It includes any method or technology that is used to determine the order of the four bases: adenine, guanine, cytosine, and thymine. Single cell DNA genome sequencing involves isolating a single cell, performing whole genome amplification (WGA), constructing sequencing libraries, and then sequencing the DNA using a next-generation sequencer (e.g., Illumina, Ion Torrent, etc.). Single cell genome sequencing is particularly of interest in the field of cancer study, as cancer cells are constantly mutating and it is of great interest to observer how cancers evolve at the genetic level. For example, single cell genome sequencing allowing for patterns of somatic mutations and copy number aberration to be observed.

Single-cell transcriptomics examines the gene expression level of individual cells in a given population by simultaneously measuring the messenger RNA (mRNA) concentration of hundreds to thousands of genes.

The purpose of single cell transcriptomics is to determine what genes are being expressed in each cell. The transcriptome is often used to quantify the gene expression instead of the proteome because of the difficulty currently associated with amplifying protein levels. Single-cell transcriptomics uses sequencing techniques similar to single cell genomics or direct detection using fluorescence in situ hybridization. The first step in quantifying the transcriptome is to convert RNA to cDNA using reverse transcriptase so that the contents of the cell can be sequenced using NGS methods, similar to what is done in single-cell genomics. Once converted, cDNA undergoes whole genome amplification (WGA), and then sequencing is performed. Alternatively, fluorescent compounds attached to RNA hybridization probes may be used to identify specific sequences and sequential application of different RNA probes will build up a comprehensive transcriptome.

Single cell transcriptomics can be used for various studies, such as, for example, gene dynamics, RNA splicing, and cell typing. Gene dynamics are usually studied to determine what changes in gene expression effect different cell characteristics. For example, this type of transcriptomic analysis has often been used to study embryonic development. RNA splicing studies are focused on understanding the regulation of different transcript isoforms. Single cell transcriptomics has also been used for cell typing, where the genes expressed in a cell are used to identify types of cells.

Single-cell proteomics is the study of proteomes (the entire complement of proteins that is or can be expressed by a cell, tissue, or organism) and their functions. The purpose of studying the proteome is to better understand the activity of cells at the single cells level. Since proteins are responsible for determining how the cell acts, understanding the proteome of single cell gives the best understanding of how a cell operates, and how gene expression changes in a cell due to different environmental stimuli. Although transcriptomics has the same purpose as proteomics it is not as accurate at determining gene expression in cells as it does not take into account post-transcriptional regulation.

There are three major approaches to single-cell proteomics: antibody based methods; fluorescent protein based methods; and mass-spectroscopy based methods. The antibody based methods use designed antibodies to bind to proteins of interest. These antibodies can be bound to fluorescent molecules such as quantum dots or isotopes that can be resolved by mass spectrometry. Since different colored quantum dots or different isotopes are attached to different antibodies it is possible to identify multiple different proteins in a single cell. Rare metal isotopes attached to antibodies, not normally found in cells or tissues, can be detected by mass spectrometry for simultaneous and sensitive identification of proteins. Another antibody based method converts protein levels to DNA levels. The conversion to DNA makes it possible to amplify protein levels and use NGS to quantify proteins. To do this, two antibodies are designed for each protein needed to be quantified. The two antibodies are then modified to have single stranded DNA connected to them that are complimentary. When the two antibodies bind to a protein the complimentary strands will anneal and produce a double stranded piece of DNA that can then be amplified using PCR. Each pair of antibodies designed for one protein is tagged with a different DNA sequence. The DNA amplified from PCR can then be sequenced, and the protein levels quantified.

In mass spectroscopy-based proteomics, there are three major steps needed for peptide identification: sample preparation; separation of peptides; and identification of peptides. Several groups have focused on oocytes or very early cleavage-stage cells since these cells are unusually large and provide enough material for analysis. Another approach, single cell proteomics by mass spectrometry (SCoPE-MS) has quantified thousands of proteins in mammalian cells with typical cell sizes (diameter of 10-15 μm) by combining carrier-cells and single-cell barcoding. Multiple methods exist to isolate the peptides for analysis. These include using filter aided sample preparation, the use of magnetic beads, or using a series of reagents and centrifuging steps. The separation of differently sized proteins can be accomplished by using capillary electrophoresis (CE) or liquid chromatograph (LC) (using liquid chromatography with mass spectroscopy is also known as LC-MS). This step gives order to the peptides before quantification using tandem mass-spectroscopy (MS/MS). The major difference between quantification methods is some use labels on the peptides such as tandem mass tags (TMT) or dimethyl labels which are used to identify which cell a certain protein came from (proteins coming from each cell have a different label) while others use not labels (quantify cells individually). The mass spectroscopy data is then analyzed by running data through databases that convert the information about peptides identified to quantification of protein levels. These methods are very similar to those used to quantify the proteome of bulk cells, with modifications to accommodate the very small sample volume. Improvements in sample preparation, mass-spec methods and data analysis can increase the sensitivity and throughput by orders of magnitude.

Single-cell metabolomics is study of chemical processes involving metabolites, the small molecule intermediates and products of metabolism, within cells. In particular, the purpose of single cell metabolomics is to gain a better understanding at the molecular level of major biological topics such as: cancer, stem cells, aging, as well as the development of drug resistance. In general the focus of metabolomics is mostly on understanding how cells deal with environmental stresses at the molecular level, and to give a more dynamic understanding of cellular functions. Accordingly, single cell metabolomics involves the study of a metabolome, which represents the complete set of metabolites in a biological cell, which are the end products of cellular processes. As generally understood, mRNA gene expression data and proteomic analyses reveal the set of gene products being produced in the cell, data that represents one aspect of cellular function. Conversely, metabolic profiling can give an instantaneous snapshot of the physiology of that cell, and thus, metabolomics provides a direct functional readout of the physiological state of an organism.

There are four major methods used to quantify the metabolome of single cells: fluorescence-based detection, fluorescence biosensors, FRET biosensors, and mass spectroscopy. The fluorescence-based detection, fluorescence biosensors, and FRET biosensors methods each use fluorescence microscopy to detect molecules in a cell. Such assays use small fluorescent tags attached to molecules of interest. However, it has been found that use of fluorescent tags may be too invasive for single cell metabolomics, and alters the activity of the metabolites. As such, the current solution to this problem is to use fluorescent proteins which will act as metabolite detectors, fluorescing whenever they bind to a metabolite of interest.

Mass spectroscopy is becoming the most frequently used method for single cell metabolomics, as there is no need to develop fluorescent proteins for all molecules of interest, and it is capable of detecting metabolites in the femtomole range. Similar to the methods discussed in proteomics, there has also been success in combining mass spectroscopy with separation techniques such as capillary electrophoresis to quantify metabolites. Another method utilizes capillary microsampling combined with mass spectrometry and ion mobility separation, which has been demonstrated to enhance the molecular coverage and ion separation for single cell metabolomics.

In preferred embodiments, a second assay may include sequencing nucleic acid from the one or more live cells having undergone the first assay to produce sequence data. In order to perform nucleic acid sequencing, methods of the disclosure further include extracting nucleic acid from the one or more live cells having undergone the first analysis for a downstream sequencing step.

Isolation, extraction or derivation of genomic nucleic acids may be performed by methods known in the art using techniques such as those described in Green & Sambrook, 2012, Molecular Cloning: A Laboratory Manual 4 edition, Cold Spring Harbor Laboratory Press, Cold Spring Harbor, NY (2028 pages), incorporated by reference. Methods may include amplifying the nucleic acid, generally carried out using polymerase chain reaction (PCR) or other technologies well known in the art (e.g., Dieffenbach, PCR Primer, a Laboratory Manual, 1995, Cold Spring Harbor Press, Plainview, NY). PCR primers can also be obtained from commercial sources such as Operon Technologies, Amersham Pharmacia Biotech, Sigma, and Life Technologies.

Figure 6:
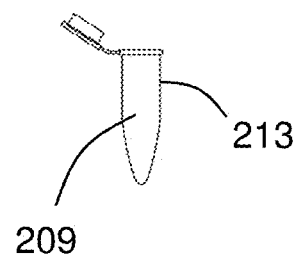
FIG. 6 diagrams a sequencing workflow consistent with the present disclosure.
Figure 6:
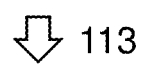
Figure 6:
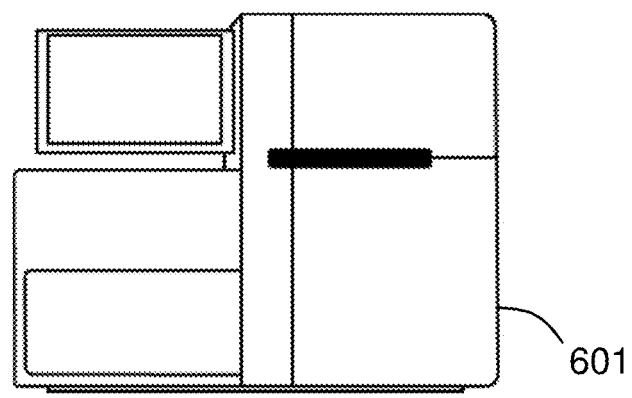
Figure 6:
Figure 6:
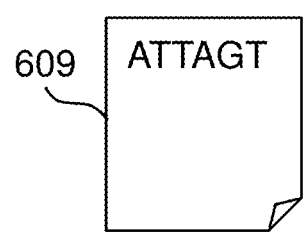

FIG. 6 shows a performing 113 an additional assay on live cells from the sample 209. The additional assays may include sequencing nucleic acid from the one or more live cells (typically, amplicons after PCR of isolated nucleic acid from sample 209) using a sequencing instrument 601 to produce sequence data 609, and, in turn, methods of the invention may include analyzing 117 the sequence data 609 (as well as the measured cancer biomarker from the first assay). The sequence data 609 can be stored in databases of the invention along with associated patient, drug, and outcome information for future analysis in determining treatment options and predicting results.

Analyzing 117 may include detecting one or more polymorphisms in the sequence data 609. Additionally, or alternatively, analyzing 117 may include mapping unique sequence reads to a reference to determine sub-chromosomal copy number variation or aneuploidy. Additionally, or alternatively, analyzing 117 may include determining expression levels in the one or more live cells. In some embodiments, analyzing 117 may further include determining tumor mutational burden (TMB). The TMB may be is determined by mapping sequence reads to a reference genome, identifying differences between the reads and the reference, and adding the identified difference to a mutation count. As previously noted, in some embodiments, the functional cancer biomarker measured in the first assay may include mass and/or mass change.

In some embodiments, analyzing 117 includes analyzing sequence data from a plurality of different cells from a sample from the patient, assigning the cells to clonal groups based on the sequence data, and measuring the functional cancer biomarker for cells from specific clonal groups. In some embodiments, the functional cancer biomarker measured in the first assay may include a mass accumulation rate. As such, in some embodiments, analyzing 117 further includes identifying mutations exclusively present in clonal groups with the highest mass accumulation rate(s) as putative driver mutations. In some embodiments, analyzing 117 includes identifying mutations whose presence does not correlate with mass accumulation rate as passenger mutations.

Sequencing may be by any method known in the art such as, for example, Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pat. Nos. 7,960,120; 7,835,871; 7,232,656; 7,598,035; 6,911,345; 6,833,246; 6,828,100; 6,306,597; 6,210,891; U.S. Pub. 2011/0009278; U.S. Pub. 2007/0114362; U.S. Pub. 2006/0292611; and U.S. Pub. 2006/0024681, each of which is incorporated by reference in their entirety.

Figure 7:
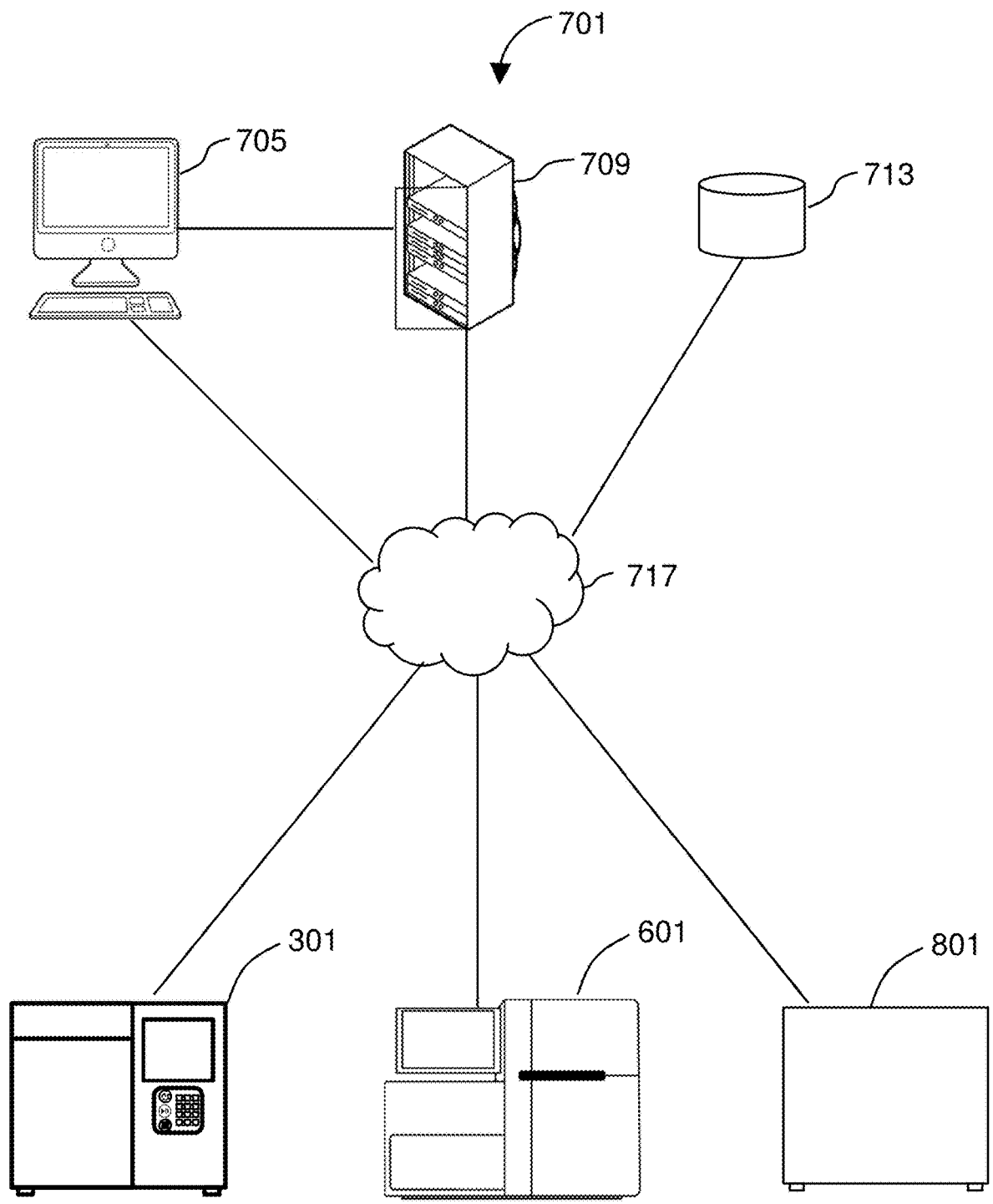
FIG. 7 shows a system for performing methods of the disclosure.

FIG. 7 is a block diagram of a system 701 according to embodiments of the invention. The system 701 may include one or more of an instrument 301 comprising a suspended microchannel resonator (SMR), a sequencing instrument 601, and any additional analysis instruments 801 for performing additional assays on the one or more cells downstream of the initial assay (performed by instrument 301), a computer 705, a server 709, and storage 713. Any of those elements may interoperate via a network 717. Any one of the instruments 301, 401, and 801 may include its own on-board computer. The computer 705 may include one or more processors and memory as well as an input/output mechanism. Where methods of the invention employ a client/server architecture, steps of methods of the invention may be performed using the server 709, which includes one or more of processors and memory, capable of obtaining data, instructions, etc., or providing results via an interface module or providing results as a file. The server 709 may be provided by a single or multiple computer devices, such as the rack-mounted computers sold under the trademark BLADE by Hitachi.

In system 701, each computer preferably includes at least one processor coupled to a memory and at least one input/output (I/O) mechanism. A processor will generally include a chip, such as a single core or multi-core chip, to provide a central processing unit (CPU). A process may be provided by a chip from Intel or AMD.

Memory can include one or more machine-readable devices on which is stored one or more sets of instructions (e.g., software) which, when executed by the processor(s) of any one of the disclosed computers can accomplish some or all of the methodologies or functions described herein. Memory devices may include one or any combination of RAM and hard drives, solid-state memories (e.g., subscriber identity module (SIM) card, secure digital card (SD card), micro SD card, or solid-state drive (SSD)), optical and magnetic media, and/or any other tangible storage medium or media. A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem. Any of the software can be physically located at various positions, including being distributed such that portions of the functions are implemented at different physical locations.

The system 701 or components of system 701 may be used to perform methods described herein. Instructions for any method step may be stored in memory and a processor may execute those instructions.

The system 701 thus includes at least one computer (and optionally one or more instruments) operable to obtain one or more live cells isolated from a sample of a patient, wherein the one or more live cells comprise at least one of a cancer cell and a cancer-related immune cell. The system 701 is further operable to perform a first assay on the one or more live cells, wherein the first assay comprises measuring a functional cancer biomarker in the one or more live cells. The system 701 is further operable to perform a second assay on the one or more live cells having undergone the first assay. The system 701 is further operable to analyze data from the second assay and the measured cancer biomarker to determine at least a stage or progression of the cancer. Using the computer 701, the system is operable to provide a report comprising any suitable patient information including identity along with information related to the cancer evaluation, including, but not limited to, specific data associated with the first and second assays, a determination of a stage or progression of cancer, and personalized treatment tailored to an individual patient's cancer.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for selecting a cancer treatment, the method comprising:
    training a machine learning system on a training data set, wherein the training data set includes patient information, therapeutic information, cancer features, and outcomes for patient, therapeutic, and cancer combinations;
    operating the machine learning system to identify correlations between therapeutics, patients, cancers, and outcomes;
    identifying, in silico, a list of therapeutics that meet predetermined criteria relating to one or more selected from the group of toxicology, efficacy, pharmacokinetics, side-effects, therapeutic interactions, patient compliance, and cost;
    obtaining a biological sample containing cancer cells from a subject;
    contacting the cancer cells with the identified therapeutics and measuring mass accumulation of the contacted cancer cells using at least one suspended microchannel resonator;
    analyzing the contacted cancer cells after measuring mass accumulation by extracting nucleic acid or protein from the contacted cancer cells and performing a biomarker assay on the extracted nucleic acid or protein to identify a cancer biomarker;
    selecting one of the identified therapeutics, based on the measured mass accumulation of the contacted cancer cells, for treating cancer in the subject;
    feeding, into the machine learning system, the patient information of the subject, selected therapeutic, cancer features of the subject, and a clinical outcome for the subject; and
    operating the machine learning system to update training of the machine learning system and update the identified correlations.

2. The method of claim 1, wherein the biological sample is from a patient having received a prior therapy for cancer.

3. The method of claim 2, wherein the predetermined criteria further comprises the prior therapy the patient has received.

4. The method of claim 1, wherein the microchannel resonator includes a channel extending through a cantilever positioned between a light source and a photodetector, wherein the light source comprises a super-luminescent diode.

5. The method of claim 1, further comprising isolating individual, live cells, from the biological sample before measuring the mass accumulation and performing the in vitro assay on the individual, live cells.

6. The method of claim 5, wherein the biological sample comprises a tissue sample.

7. The method of claim 6, wherein the tissue sample is a biopsy sample.

8. The method of claim 7, where the biopsy sample is obtained by fine needle biopsy and comprises less than 50,000 cancer cells.

9. The method of claim 1, wherein measuring the mass accumulation is performed within about 48 hours after obtaining the biological sample.

10. The method of claim 1, wherein measuring the mass accumulation is performed within about 24 hours after obtaining the biological sample.

11. The method of claim 1, wherein measuring the mass accumulation is performed within about 6 hours after obtaining the biological sample.

12. The method of claim 1, wherein the suspended microchannel resonator further comprises a photodetector which is connected to a processing chip and wherein the photodetector converts an optical signal from the light source to a voltage signal sent the processing chip.

13. The method of claim 12, wherein the suspended microchannel resonator is provided in one of an array of cantilevers and wherein the processing chip implements a plurality of parallel phase-locked loops that each both demodulate and drive one respective cantilever of the array of cantilevers.

14. The method of claim 13, wherein the processing chip comprises a field-programmable gate array (FPGA).

15. The method of claim 13, wherein the array comprises at least one piezo-ceramic actuator used for actuation of the cantilevers.

16. A method for selecting a cancer treatment, the method comprising:
    training a machine learning system on a training data set, wherein the training data set includes patient information, therapeutic information, features of cancer cells, and outcomes for patient, therapeutic, and cancer combinations;
    operating the machine learning system to identify correlations between therapeutics, patients, cancers, and outcomes;
    identifying, in silico, a list of therapeutics that meet predetermined criteria relating to one or more selected from the group of toxicology, efficacy, pharmacokinetics, side-effects, therapeutic interactions, patient compliance, and cost;
    obtaining a biological sample containing cancer cells from a subject;
    contacting the cancer cells with the identified therapeutics and measuring mass accumulation of the contacted cancer cells using at least one suspended microchannel resonator;
    selecting a first therapeutic from the identified therapeutics, based on the measured mass accumulation of the contacted cancer cells, for treating cancer in the subject;
    feeding, into the machine learning system, patient information of the subject, therapeutic information of the subject, cancer features of the subject, a clinical outcome of the subject for the first therapeutic, and mass accumulation measurements from a second therapeutic from the identified therapeutics; and
    operating the machine learning system to update training of the machine learning system and update the identified correlations.

17. A method for selecting a cancer treatment, the method comprising:
    contacting cancer cells from a first patient with a panel of therapeutics and obtaining mass accumulation measurements of the cancer cells using a suspended microchannel resonator;
    training a machine learning system with a data set that includes first patient information, features of the cancer cells from the first patient, and therapeutic information of the first patient as inputs, and the mass accumulation measurements and patient response data of the first patient as outcomes; and
    operating the machine learning system to identify a therapeutic useful for treating cancer in a second patient based on second patient information and features of cancer cells from the second patient.

* * * * *